(12) United States Patent
Hsieh

(10) Patent No.: US 7,696,329 B2
(45) Date of Patent: Apr. 13, 2010

(54) IMMUNOGLOBULIN PEPTIDES AGAINST HEATED BOVINE BLOOD

(75) Inventor: Yun-Hwa Peggy Hsieh, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 506 days.

(21) Appl. No.: 11/616,427

(22) Filed: Dec. 27, 2006

(65) Prior Publication Data

US 2007/0298517 A1 Dec. 27, 2007

Related U.S. Application Data

(60) Provisional application No. 60/805,685, filed on Jun. 23, 2006.

(51) Int. Cl.
C07K 16/18 (2006.01)
C07K 17/00 (2006.01)

(52) U.S. Cl. .................... 530/388.1; 530/391.1; 422/61

(58) Field of Classification Search ........................ None
See application file for complete search history.

(56) References Cited

U.S. PATENT DOCUMENTS

| | | | |
|---|---|---|---|
| 4,609,893 A | 9/1986 | Cornish | |
| 4,713,325 A | 12/1987 | Lutz | |
| 4,714,681 A | 12/1987 | Reading | |
| 4,716,111 A | 12/1987 | Osband et al. | |
| 4,716,117 A | 12/1987 | Kuo et al. | |
| 4,720,459 A | 1/1988 | Winkelhake | |
| 6,288,215 B1 | 9/2001 | Hsieh | |
| 6,423,506 B1 | 7/2002 | Hsieh | |
| 6,692,930 B2 | 2/2004 | Hsieh | |

OTHER PUBLICATIONS

Hsieh et al. "Monoclonal Antibodies Specific to Thermostable Proteins in Animal Blood" J. Agric. Food Chem. 2007, 55, 6720-6725.*
Castilla et al. (2005) Detection of prions in blood, Nature Medicine, vol. 11, No. 9, pp. 982-985.
Clackson et al. (1991) Making antibody fragments using phage display libraries, Nature, vol. 352, pp. 624-628.
Cwirla, et al. (1990) Peptides on phage: A vast library of peptides for identifying ligands, Proc. Natl. Acad. Sci. USA, vol. 87, pp. 6378-6382.
Holliger, et al. (1993) "Diabodies": Small bivalent and bispecific antibody fragments, Proc. Natl. Acad. Sci. USA, vol. 90, pp. 6444-6448.
Houston et al. (2000) Transmission of BSE by blood transfusion in sheep, Lancet, vol. 356, pp. 999-1000.
Kashyap, M. L. et al. (1977) Radioimmunoassay of Human Apolipoprotein CII, Journal of Clinical Investigation, vol. 60, pp. 171-180.
Koren, E. et al. (1986) Characterization of a monoclonal antibody that binds equally to all apolipoprotein and lipoprotein forms of human plasma apolipoprotein B. I. Specificity and binding studies, Biochim. Biophys. Acta 876, pp. 91-100.
Krodel, E. et al. (1991) Technical Challenges in the Development of the CIBA Corning ACS:180 Benchtop Immunoassay Analyzer; Bioluminescence and Chemiluminescence, John Wiley and Sons Inc. New York, pp. 107-110.
Lowman, et al. (1991) Selecting High-Affinity Binding Proteins by Monovalent Phage Display, Biochemistry, 30, pp. 10832-10838.
Taylor, et al. (2000) Infectivity in the blood of mice with a BSE-derived agent, J. Hosp. Infect, vol. 46, pp. 78-79.
Weeks et al. (1983) Two-Site Immunochemiluminometric Assay for Human α1 -Fetoprotein, Clin. Chem. 29/8, pp. 1480-1483.
Wood, P. (1991) Heterogeneous fluoroimmunoassay, Principles and Practice of Immunoassay, Stockton Press, New York, pp. 365-392.
Parmley, Stephen F., et al. (1989) Filamentous Fusion Phage Cloning Vectors for the Study of Epitopes and Design of Vaccines, Adv. Exp. Med. Biol., 251, pp. 215-218.
Hoogenboom, H.R., et al., "Mutli-Subunit Proteins on the Surface of Filamentous Phage: Methodologies for Displaying Antibody (Fab) Heavy and Light Chains," Nucleic Acids Research vol. 19, No. 15, pp. 4133-4137 (1991).
Harlow, E., et al., "Using Antibodies, A Laboratory Manual", Cold Spring Harbor Laboratory, N.Y., Chapters 3 and 4, pp. 39-97 (1996).
Campbell, A.M., "Monoclonal Antibody and Immunosensor Technology," Laboratory Techniques in Biochemistry And Molecular Biology, Vol. 23, Elsevier, Amsterdam, Chapters 4-8, pp. 139-236 (1991).

* cited by examiner

*Primary Examiner*—Mark L Shibuya
*Assistant Examiner*—Christine Foster
(74) *Attorney, Agent, or Firm*—Vedder Price P.C.; Ajay A. Jagtiani

(57) ABSTRACT

The present invention is related to immunoglobulin peptides that recognize a thermostable antigen from bovine blood. The invention also provides methods for determining the presence of bovine blood in a food sample or an animal feed sample.

13 Claims, 22 Drawing Sheets

% BOVINE PLASMA MEAL
IN AUTOCLAVED PORCINE BLOOD

FIG. 13

*(Graph: Absorbance at 415nm vs % whole bovine blood powder in spray-dried porcine plasma (v/v). Values approximately: 0% → 0.13; 0.1% → 0.14; 0.5% → 0.19; 1% → 0.24; 3% → 0.41; 5% → 0.49; 10% → 0.59.)*

IMMUNOGLOBULIN PEPTIDES AGAINST HEATED BOVINE BLOOD

REFERENCE TO RELATED APPLICATIONS

This patent application claims priority to Provisional Patent Application Ser. No. 60/805,685, filed on Jun. 23, 2006, which is incorporated herein by reference.

FIELD OF THE INVENTION

The present invention is directed to immunoglobulin peptides which recognize a thermostable antigen from bovine blood. The invention also relates to a kit containing one or more of such peptides. Further provided are methods for determining the presence of bovine blood in a food sample or an animal feed sample.

The present invention is directed to immunoglobulin peptides which recognize a thermostable antigen from bovine blood. The invention also relates to a kit containing one or more of such peptides. Further provided are methods for determining the presence of bovine blood in a food sample or an animal feed sample.

BACKGROUND OF THE INVENTION

Transmissible spongiform encephalopathy (TSE) agents induce fatal neurodegenerative diseases in mammalian species and humans. The TSE group in animals includes scrapie in sheep and goat, bovine spongiform encephalopathy (BSE) in cattle, feline spongiform encephalopathy, transmissible mink encephalopathy, and chronic wasting disease (CWD) in wild ruminants. Among them, BSE, commonly known as mad cow disease, has brought enormous economic consequences since its first incidence in the United Kingdom in 1986. The BSE outbreaks peaked in the United Kingdom in 1993 at almost 1000 new cases per week, and it caused more than 182,000 cases between 1988 and 2002. In addition, the emergence of a new variant form of Creutzfeldt-Jakob Disease (vCJD) in humans in the United Kingdom has been proposed to be possibly linked with BSE.

Meat and bone meal, an ingredient of animal feed, contaminated with a TSE agent was believed to be the major vehicle of BSE transmission, according to epidemiological inquiry. Meat and bone meal has been produced by rendering the discarded animal fat, bones, offal, and whole carcasses from bovine, ovine, porcine, and poultry. Although the use of meat and bone meal in cattle as a nitrogen supplement had been a common practice for several decades, changes in rendering operations in the 1970s and 1980s may have allowed the survival of the contagious agents that can be transmitted to the cattle through the meat and bone meal. The oral route was the major mode of natural transmission of BSE to cattle. To prevent the spread of BSE, the European Union in 1988 banned the inclusion of ruminant-derived proteins in animal feed. The U.S. Food and Drug Administration also introduced the feed ban in 1997 to prohibit the use of proteins derived from mammalian tissues in feeding ruminants. Nevertheless, the use of mammalian blood and blood products and any products having only protein of porcine or equine origin in ruminant feed products is still allowed. However, recent evidence indicates that blood also carries some level of infectivity for TSE since transmission of TSE has been demonstrated through inoculation of blood in animals infected with various strains of TSE (see, e.g., Castilla et al., Nat. Med., Vol. 11, pp. 982-985, 2005; Houston et al., Lancet, Vol. 356, pp. 999-1000, 2000; and Taylor et al., J. Hosp. Infect., Vol. 46, pp. 78-79, 2000). In addition to being used in animal feed, animal blood is used as a source of human food in many countries, usually in the form of blood sausages, pudding, soup, bread and crackers. Even in the U.S., blood is used, e.g., in sausage products to enhance color, in bakery products as an egg substitute or in liquid foods as a clarifying agent.

Although prohibited, meat and bone meal from ruminant origin may still enter cattle diets accidentally as a result of cross-contamination during feed mixing at the feed mills, transportation, storage, or the farm. Indeed, the U.S. Food and Drug Administration found very low levels of prohibited meat and bone meal residues in the feedlot resulting from misformulation of the animal feed supplement at feed mills. In addition, although bovine blood and plasma are currently acceptable for certain uses, their future is uncertain due to changing attitudes of producers, blenders, and consumers who would like to have products that are "free" of bovine blood and plasma products. Feed blenders and manufacturers usually acquire these blood and plasma products from renderers who process or transport products from both ruminants (cattle, buffalo, sheep, goats, deer, elk, and antelopes) and nonruminants (pigs, and horses). Thus, care must be taken to ensure that cross-contamination does not occur in the blending or manufacturing process.

Tools that permit enforcement of the meat and bone meal bans to eradicate BSE are becoming increasingly important for compliance with animal byproduct regulation. Furthermore, the accurate labeling of meat products is mandated and monitored by the United States Department of Agriculture (USDA) as well as by state and local governments. Mixing undeclared species in meat products is illegal under Food Labeling Regulations.

To date, there are technical limitations in detecting prohibited residues in animal feed because most of the analytical methods cannot distinguish between allowable and prohibited bovine materials. Several methods have been developed to identify meat species including electrophoresis, chromatography, DNA hybridization, and immunoassays. Immunological techniques, including agar-gel immunodiffusion (AGID) and enzyme-linked immunosorbent assay (ELISA) are most commonly applied for meat species identification.

There are several disadvantages to the AGID method. Concentrated antiserum preparations are required to obtain visible precipitin lines in AGID. Obtaining the antiserum is expensive in large-scale testing. Furthermore, the sensitivity of AGID is variable. Usually ten percent or more contamination must be present to detect adulteration with this method. Lastly, AGID cannot be used for species identification in cooked meat because of the shortage of commercial antiserum specific to cooked meats.

With respect to blood protein detection, the currently used methods such as spectrophotometry, the Takayama confirmatory test and immunochemical methods also exhibit several limitations. This is in part due to the fact that these assays are mainly based on heat-labile blood proteins, resulting in lack of species specificity and making them unusable for detection of blood in heat-treated samples such as cooked food or blood meal in animal feed.

BRIEF SUMMARY OF THE INVENTION

Among the various aspects of the present invention are immunoglobulin peptides which bind an antigen from bovine blood. The immunoglobulin peptides may be used, for example, in a screening assay to identify or detect exogenous blood.

Another aspect of the present invention is a method for determining the presence of bovine blood in a sample. The method comprises combining the sample with an immunoglobulin peptide which binds an antigen from bovine blood and determining whether any antigen from the sample was bound by the immunoglobulin peptide.

Still another aspect of the present invention is a method for determining presence of bovine blood in a food sample or an animal feed sample, which comprises coating a carrier surface with a sample potentially containing bovine blood antigen; contacting the coated surface with an immunoglobulin peptide having affinity for a thermostable bovine blood antigen; and determining whether the immunoglobulin peptide bound to the coated surface.

Other objects and features will be in part apparent and in part pointed out hereinafter.

BRIEF DESCRIPTION OF THE DRAWINGS

FIG. 13 is a graph depicting the detection of autoclaved bovine blood in autoclaved porcine blood by antibodies 6G12 (capture antibody) and 3D6 (biotin conjugated detection antibody) when used in a sandwich ELISA as more fully described in Examples 2 and 3.

Figure 1:
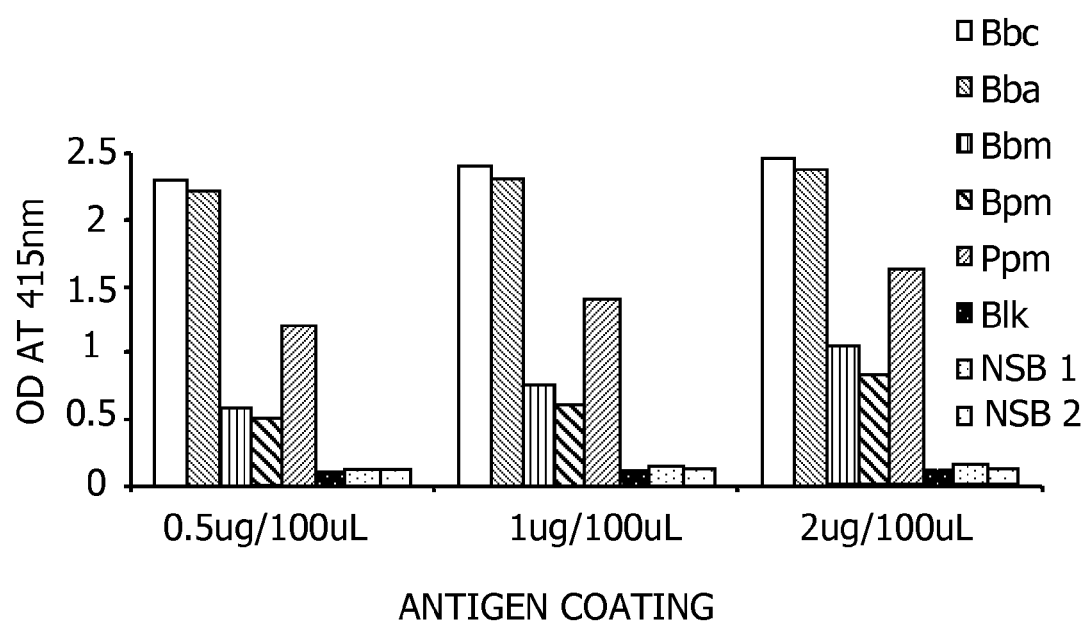
FIG. 1 is a graph depicting the effect of antigen coating (0.5 µg/100 µL) on signals for commercial feeds using 1B4 antibody as more fully described in Examples 2 and 3. Dilutions of 1B4 and secondary antibody anti-IgG-HRP(Fc) were performed at 1:3 in 1% BSA-PBST.
Figure 2:
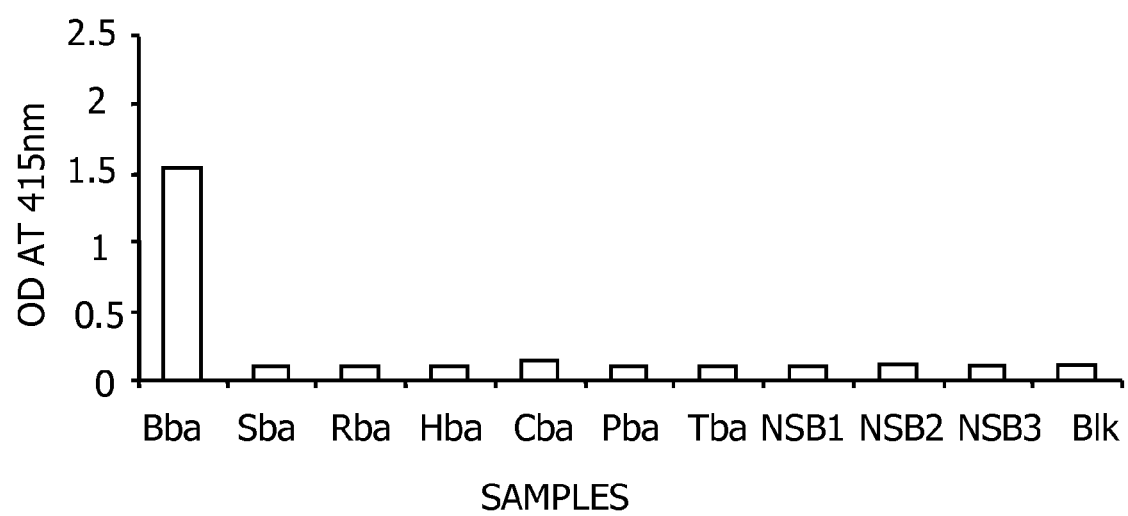
FIG. 2 is a graph depicting species specificity of antibodies 3D6 and 6G12 when used in a sandwich ELISA as more fully described in Examples 2 and 3. Bba=autoclaved bovine blood, Sba=autoclaved sheep blood, Rba=autoclaved rabbit blood, Hba=autoclaved horse blood, Cba=autoclaved chicken blood, Pba=autoclaved pork blood, Tba=autoclaved turkey blood, NSB1=non-specific binding 1(antibody only), NSB2=non-specific binding 2(antigen only), Blk=blank
Figure 3A:
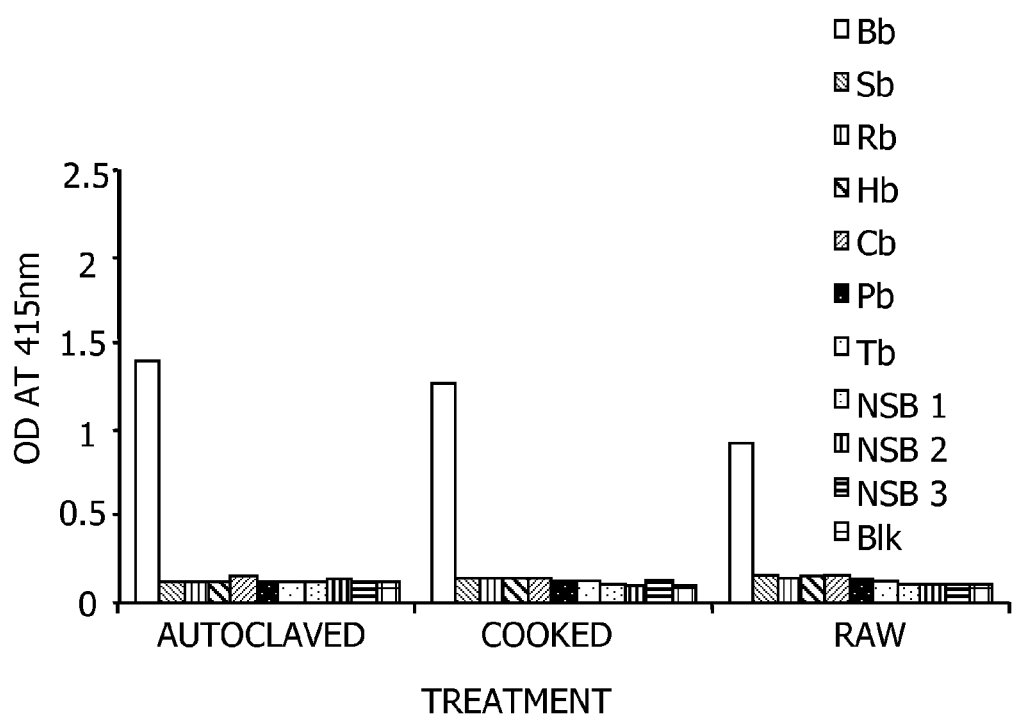
FIGS. 3A and 3B are graphs depicting the effect of heat treatment on the species specificity of antibodies 6G12 (capture antibody) and 3D6 (biotin conjugated detection antibody) when used in a sandwich ELISA with autoclaved, cooked and raw meat as more fully described in Examples 2 and 3. Bb=bovine blood, Sba=sheep blood, Rba=rabbit blood, Hba=horse blood, Cba=autoclaved chicken blood, Pba=pork blood, Tba=turkey blood, NSB1=non-specific binding 1(antibody only), NSB2=non-specific binding 2(antigen only), Blk=blank
Figure 3B:
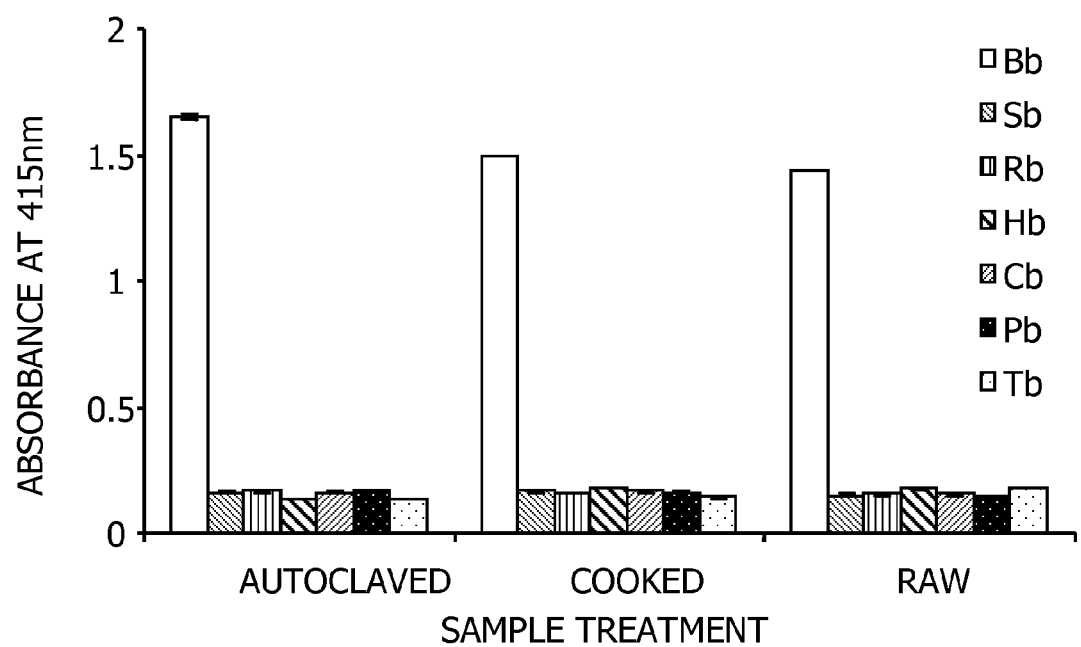
Figure 4:
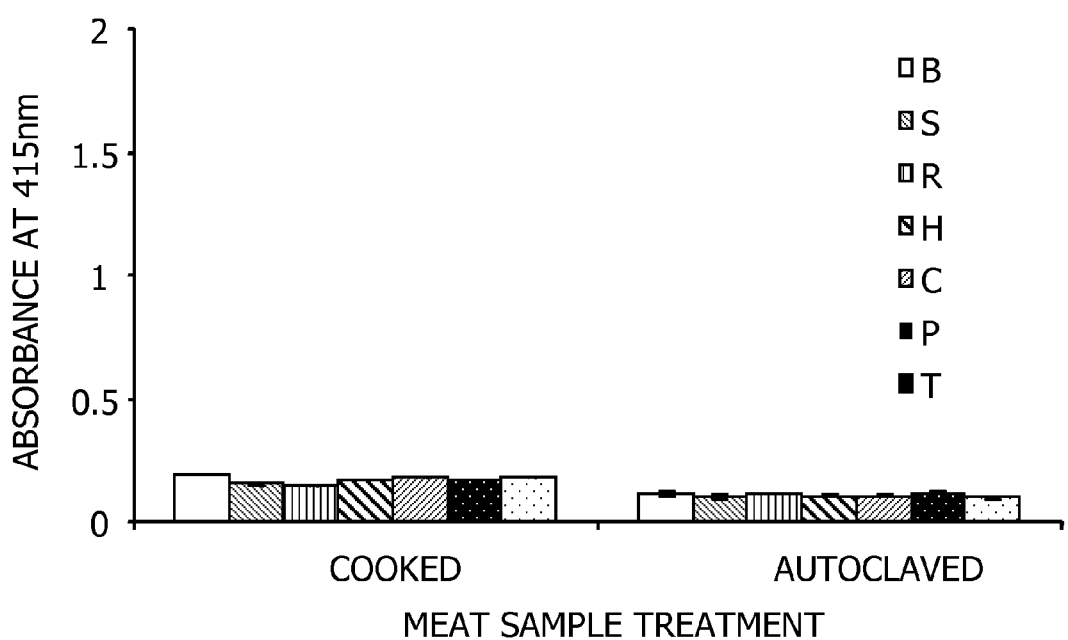
FIG. 4 is a graph depicting the cross-reactivity antibodies 6G12 (capture antibody) and 3D6 (biotin conjugated detection antibody) when used in a sandwich ELISA with cooked and autoclaved meat (flesh) proteins as more fully described in Examples 2 and 3. B=beef, S=sheep, R=rabbit, C=chicken, P=pork and T=turkey.
Figure 5A:
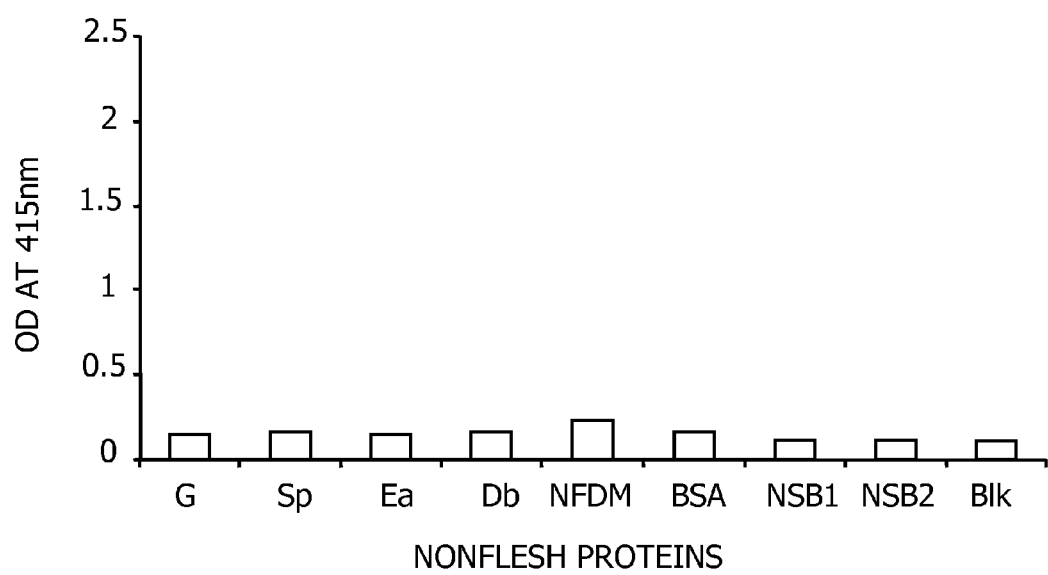
FIGS. 5A and 5B are graphs depicting the cross reactivity of antibodies 6G12 (capture antibody) and 3D6 (biotin conjugated detection antibody) when used in a sandwich ELISA with non-flesh proteins as more fully described in Examples 2 and 3. G=gelatin, S or Sp=soy protein concentrate, Ea=egg albumin, NFDM-non-fat dry milk, BSA=bovine serum albumin, NSB1=non-specific binding 1(antibody only), NSB2=non-specific binding 2(antigen only), Blk=blank
Figure 5B:
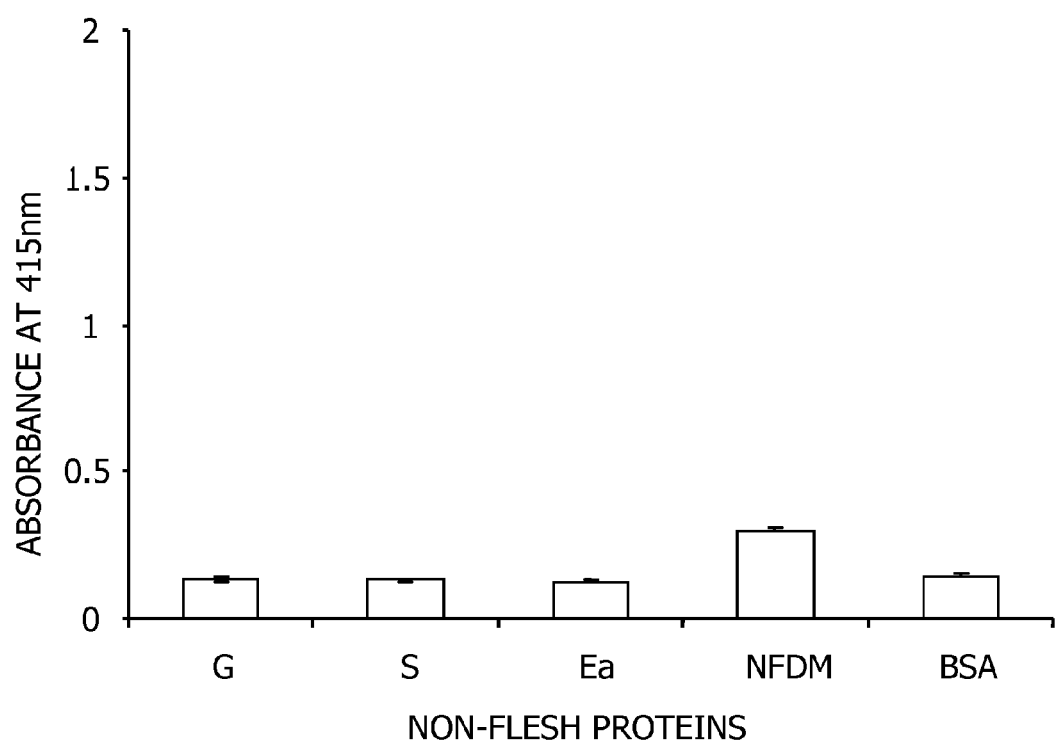
Figure 6:
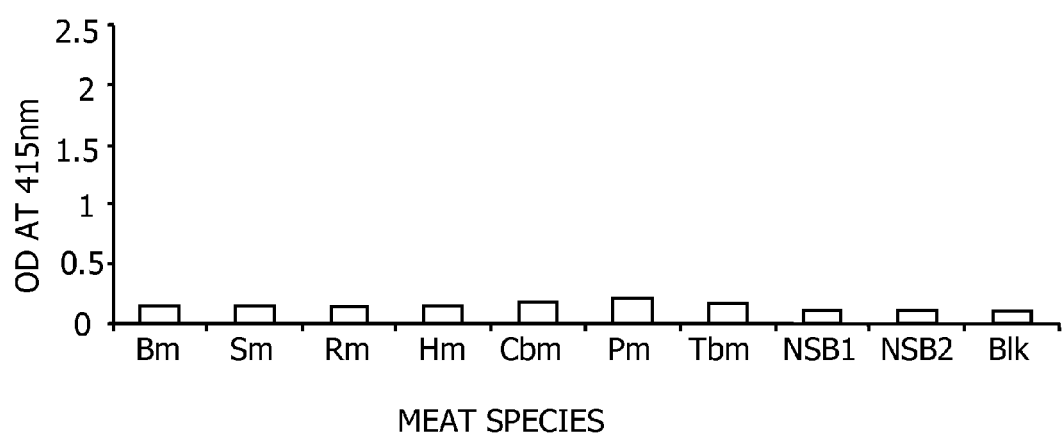
FIG. 6 is a graph depicting the cross reactivity of antibodies 6G12 (capture antibody) and 3D6 (biotin conjugated detection antibody) when used in a sandwich ELISA with flesh proteins as more fully described in Examples 2 and 3. Bm=bovine meat, Sm=sheep meat, Rm=rabbit meat, Hm=horse meat, Cm=_chicken meat, Pm=porcine meat, Tm=_turkey meat, NSB1=non-specific binding 1(antibody only), NSB2=non-specific binding 2(antigen only), Blk=blank
Figure 7A:
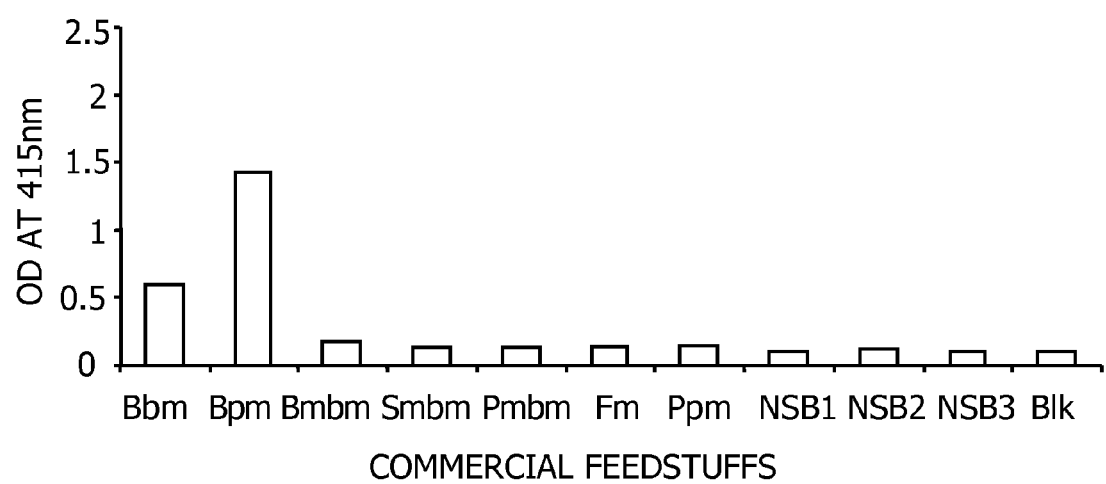
FIGS. 7A and 7B are graphs depicting the performance of antibodies 6G12 (capture antibody) and 3D6 (biotin conjugated detection antibody) when used in a sandwich ELISA with commercial feed stuffs as more fully described in Examples 2 and 3. Bbp=whole bovine blood powder, Bpm=spray-dried bovine plasma, Ppm=spray-dried porcine plasma, Smbm=sheep meat bone meal, Bmbm=bovine meat bone meal, Pmbm porcine meat bone meal, Fm=feather meal.
Figure 7B:
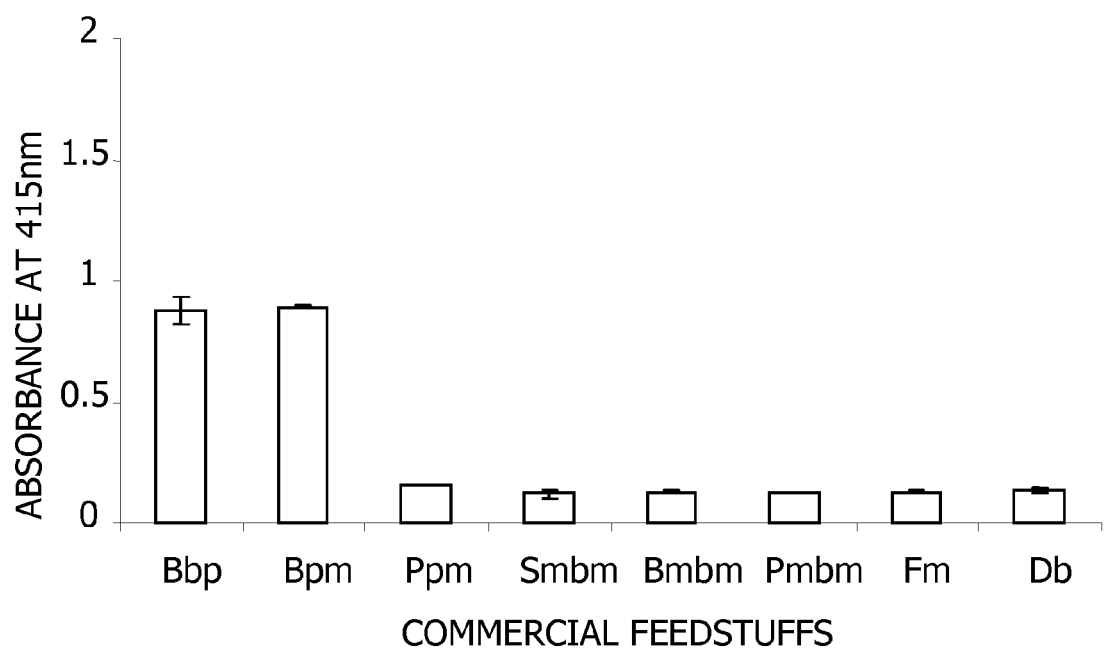

Other objects and features will be in part apparent and in part pointed out hereinafter.

DETAILED DESCRIPTION OF THE PREFERRED EMBODIMENTS

Advantageously, immunoglobulin peptides have been developed which specifically bind antigens in bovine blood. These peptides may be used in assays for detecting bovine blood in food, animal feed, or other materials, and to identify bovine species in forensic, biological, or agricultural sciences. Advantageously, the immunoglobulin peptides are specific for bovine blood antigens even after a heat treatment of the antigens. For example, monoclonal antibodies of the present invention can detect bovine blood in a sample even after the sample has been sterilized to 121° C. for 15 minutes. Thus, the ability of these immunoglobulin peptides to react with raw, cooked and autoclaved bovine blood indicates that the antigen is thermostable, allowing for the use of these peptides in a variety of the different assays.

The immunoglobulin peptides of the present invention are highly specific for bovine blood. For example, the immunoglobulin peptides detect bovine blood in a sample, wherein the sample contains less than 3 wt. % bovine blood or tissue. In one embodiment, the immunoglobulin peptides detect bovine blood in a sample, wherein the sample contains less than 2 wt. % bovine blood or tissue. Preferably, the immunoglobulin peptides detect bovine blood in a sample, wherein the sample contains less than 1 wt. % bovine blood or tissue. In one embodiment, the immunoglobulin peptides exhibit some cross-reactivity with blood samples of other mammalian species, such as ovine, equine or porcine. The cross-reactivity may be desirable, e.g. in immunoassays with broad specificity for screening a number of targeted materials with a single test. By way of example, a blood bovine specific antibody, which is cross-reactive with ovine blood protein may find application in assaying whether an animal feed sample contains any blood proteins of ruminant origin. As can be seen from Table 1, three antibodies (1B4, 2B11, 3D6) of the present invention exhibit reactivity to blood proteins from two or more mammalian species of bovine, ovine, porcine, equine or rabbit origin, whereas four antibodies (1H9, 6F10, 6G12 and 7F6) react to blood proteins of ruminant species (bovine, ovine). In another embodiment, the immunoglobulin peptides advantageously exhibit little or no cross-reactivity with other bovine tissues or blood proteins from other animal species. For example, antibody 6E1 only recognizes bovine blood proteins.

Advantageously, the immunoglobulin peptides detect bovine blood even after heating or autoclaving treatment. By way of example, immunoglobulin peptides, such as for example, monoclonal antibodies, of the present invention detect bovine blood after heating a sample containing bovine blood to 100° C. for 15 minutes or even autoclaving it at 121° C. for 15 minutes.

Capture Assay

A capture assay of the present invention employs an immunoglobulin peptide to bind a bovine blood antigen from the sample. The assays can be conducted using any procedure selected from the variety of standard assay protocols generally known in the art. In general, the assay is constructed so as to rely on the interaction of the immunoglobulin peptide, bovine blood antigen, and a label (or reporter molecule). In one embodiment, the assay detects the formation of a complex between the immunoglobulin peptide and bovine blood antigen indirectly; for example, a competitive binding assay may be used in which label is bound to a composition also having affinity for the immunoglobulin peptide. In another embodiment, the assay detects the formation of a complex between the immunoglobulin peptide and bovine blood antigen directly; for example, a sandwich assay may be employed in which an immunoglobulin peptide capture agent is bound to the carrier, and a labeled binding agent, also having affinity for the bovine blood antigen is used to confirm the binding of antigen by the capture immunoglobulin peptide. The specific design of the assay protocol is open to a wide variety of choice, and several clinical assay devices and protocols are available in the art. In addition, the reaction can be quantitized by comparing against a standard curve derived from a known amount(s) of non-tagged molecules in both indirect and direct detection methodologies.

In one embodiment, an indirect capture assay involves immobilizing an immunoglobulin peptide on a carrier (e.g., solid support or substrate), contacting the coated carrier with the sample, reacting the remainder of binding sites on the carrier with a labeled binding agent specific for the immunoglobulin peptide, and detecting the label. The more bovine blood antigen in the sample, the less tagged binding agent can attach to a given amount of the immunoglobulin peptide on the carrier (the labeled binding agent is usually supplied in saturation compared to the amount of capture agent).

In one embodiment, a direct capture assay involves immobilizing a capture immunoglobulin peptide on a carrier, contacting the coated carrier with the sample, adding labeled immunoglobulin peptide (which may be the same as the capture immunoglobulin peptide or another binding agent having affinity for bovine blood antigens), and detecting the label. For direct detection assays, the more thermostable bovine blood antigen in the sample, the more labeled immunoglobulin peptide can attach to the thermostable bovine blood antigen which is in turn bound to the immunoglobulin peptide on the carrier (the labeled binding agent is usually supplied in saturation). For example, the sample, or a dilution thereof, is applied to the immunoglobulin peptide-coated carrier under conditions in which the immunoglobulin peptide capture agent binds molecules that display the antigen of interest. The volume of sample is such that the amount of immobilized immunoglobulin peptide on the carrier is in excess to the expected amount of bovine blood antigen in the sample. Suitable conditions are, for example, incubation of the potential bovine blood containing sample for about two to three hours at about 37° C. After allowing sufficient time for binding of thermostable bovine blood antigen to the immunoglobulin peptide, the remaining sample is then washed away.

In an alternative embodiment, a direct capture assay may involve immobilizing the sample on a carrier and contacting the coated carrier with labeled immunoglobulin peptide having specificity for bovine blood antigen. The presence or amount of labeled immunoglobulin peptide bound to the coated carrier may then be correlated directly with the presence or even amount of bovine blood antigen on the coated carrier.

The capture assays of the present invention can thus be used to detect bovine blood in a sample of food for human or domesticated animal consumption. In one embodiment, a food sample is any foodstuff used for human consumption such as, for example, fresh or canned meat, blood sausage, soups, bakery products, such as breads and cakes, crackers, butter, wines, and cheeses. Alternatively, a food sample or ingredient for animal feed for a domesticated animal may be assayed for the presence (or even amount) of bovine blood, including spray dried blood, bovine plasma, and tissues or substances containing the same; the feed or ingredient may be intended for use, for example, with bovine, swine, and poultry.

Carrier

In general, the carrier may be any of a wide range of suitable substrates onto which the immunoglobulin peptide capture agent or bovine blood antigens will attach, usually by electrostatic forces. The carrier can be, for example, plastic or glass material in the form of a tray, bead, or tube, or the carrier can be a suitable membrane of nylon or nitrocellulose. Preferably, the carrier is a plastic microtiter well. Immobilization onto the carrier can occur, for example, by incubating the immunoglobulin peptide capture agent or sample in the microtiter well overnight at about 4° C.

After immobilization, excess immunoglobulin peptide capture agent or sample is removed, and the carrier is usually blocked with a blocking buffer. For example, the carrier can be blocked with a BSA/PBS buffer solution containing sodium azide for a period of time from about 2 hours to overnight in a humid atmosphere at room temperature. After blocking, the carrier can be washed with a suitable buffer.

Capture Agent

An immunoglobulin peptide capture agent coating a solid phase material preferably binds a sufficient quantity of bovine blood antigen, within a relatively short period of time (approximately several minutes), and retain the captured antigen during subsequent washing and detection of labeled agents. The density of the immunoglobulin peptide on the carrier can be, for example, from about 1 µg/ml to about 50 µg/ml, and more generally around 20 µg/ml. The amount of immunoglobulin peptide capture agent immobilized on the carrier ideally is in excess of the expected amount of thermostable bovine blood antigen in the sample. Calculating the amount of immunoglobulin peptide to be immobilized on the carrier as a function of the expected concentration of thermostable bovine blood antigen in the sample and the volume of sample delivered is well within the skill in the art.

Immunoglobulin peptide capture agents include, for example, polyclonal antibodies, monoclonal antibodies, and antibody fragments such as proteolytically cleaved antibody fragments and single chain Fv antibody fragments, as further discussed below. In a preferred embodiment, the immunoglobulin peptide is a monoclonal antibody.

Labeled Binding Agent

After a complex of the bovine blood antigen and the capture immunoglobulin peptide is formed, the carrier is combined with a labeled binding agent. The target of the labeled binding agent will depend upon whether indirect or direct detection means are employed.

In indirect detection assays, the resulting bovine blood antigen-immunoglobulin peptide complex is further reacted with a binding agent that has affinity for the immunoglobulin peptide, where the binding agent is attached to an easily assayable tag. The binding agent preferably binds with high affinity to immobilized immunoglobulin peptide capture agent not bound by thermostable bovine blood antigen from the sample but does not bind to immobilized immunoglobulin peptide capture agent already bound by thermostable bovine blood antigen from the sample.

In direct detection assays, the resulting thermostable bovine blood antigen-immunoglobulin peptide complex is further reacted with a binding agent that has affinity for the thermostable bovine blood antigen, where the binding agent is attached to an easily assayable tag. Direct detection binding agents preferably include an immunoglobulin peptide that displays binding specificity for the thermostable bovine blood antigen, wherein the labeled immunoglobulin peptide is the same immunoglobulin peptide as that used as the capture agent or is a second immunoglobulin peptide also having affinity for the thermostable bovine blood antigen.

Immunoglobulin peptides can be used as capture agents and/or binding agents. Immunoglobulin peptides include, for example, polyclonal antibodies, monoclonal antibodies, and antibody fragments. Immunoglobulin peptides used as capture agents are immobilized on a substrate surface, as described above. Immunoglobulin peptides used as binding agents have easily assayed labels or tags affixed, as described above.

The following describes generation of immunoglobulin peptides, specifically bovine blood antigen antibodies, via methods that can be used by those skilled in the art to make other suitable immunoglobulin peptides having similar affinity and specificity which are functionally equivalent to those used in the Examples.

Hybridoma technology permits one to explore the entire antibody producing B lymphocyte repertoire of the immune system and to select unique antibody producing cells that produce antibodies having unique binding characteristics. The production of monoclonal antibodies can be more controlled than production of polyclonal antisera since polyclonal antisera contain numerous antibody populations each having varying specificity and sensitivity characteristics that are the products of numerous responding B cell clones. MAb reagents are also homogeneous with a defined specificity. The use and appropriate selection of hybridoma cell lines provides MAb reagents that offer unique performance characteristics to the test system and consistency of the methods that utilize them.

MAbs can be screened or tested for specificity using any of a variety of standard techniques, including Western Blotting (Koren, E. et al. (1986) Biochim. Biophys. Acta 876:91-100) and enzyme-linked immunosorbent assay (ELISA) (Koren, E. et al. (1986) Biochim. Biophys. Acta 876:91-100).

Methods for the preparation of the antibodies of the present invention are generally known in the art. See, for example, Antibodies, A Laboratory Manual, Ed. Harlow & David Lane (eds.) Cold Spring Harbor Laboratory, New York (1988), as well as the references cited therein. Standard reference works setting forth the general principles of immunology include: Klein, J. Immunology: The Science of Cell-Noncell Discrimination, John Wiley & Sons, New York (1982); Dennett, R. et al. Monoclonal Antibodies, Hybridoma: A New Dimension In Biological Analyses Plenum Press, New York (1980); and Campbell, A. "Monoclonal Antibody Technology," Laboratory Techniques In Biochemistry And Molecular Biology, Vol. 13, Burdon et al. (eds.), Elsevier, Amsterdam (1984). See also, U.S. Pat. Nos. 4,609,893; 4,713,325; 4,714,681; 4,716,111; 4,716,117; and 4,720,459.

Any method can be used to generate antibodies, including but not limited to methods that elicit production of monoclonal antibodies. In one embodiment, animals such as mice are inoculated with the immunogen in adjuvant, and spleen cells are harvested and mixed with a myeloma cell line, such as P3X63Ag8,653. The cells are induced to fuse by the addition of polyethylene glycol. Hybridomas are chemically selected by plating the cells in a selection medium containing hypoxanthine, aminopterin and thymidine (HAT). Hybridomas are subsequently screened for the ability to produce anti-rendered animal byproduct monoclonal antibodies. Hybridomas producing antibodies are cloned, expanded and stored frozen for future production.

In another embodiment, antibodies are generated by immunizing an animal with an immunogenic amount of the antigen emulsified in an adjuvant such as Freund's complete adjuvant, administered over a period of weeks in intervals ranging between two weeks and 6 weeks. In a some embodiments, the method includes a first immunization in Freund's complete adjuvant and subsequent immunizations in Freund's incomplete adjuvant (at biweekly to monthly intervals thereafter) then isolating the antibodies from the serum, or fusing spleen from the animal cells to myeloma cells to make hybridomas which express the antibodies in culture. In some embodiments, test bleeds are taken at fourteen day intervals between the second and third immunizations and production bleeds at monthly intervals thereafter.

In one embodiment, the immunoglobulin peptides of the present invention are monoclonal antibodies of the IgG class. Exemplary IgG monoclonal antibodies include, for example, monoclonal antibodies selected from the group consisting of 1B4.B12.E12 (1B4), 1H9.B5.D9 (1H9), 2B11.F3.B9 (2B11), 3D6.C7.G9 (3D6), 6E1.E5.D2.B9 (6E1), 6F10.A10.B8.A11 (6F10), 6G12.G1.A9 (6G12) and 7F6.C1.H11 (7F6), produced by hybridoma cell lines deposited as ATCC Nos. PTA-9870, PTA-9869, PTA-9868, PTA-9867, PTA-9982, PTA-9983, PTA-9985 and PTA-9984, respectively. Biological deposits of hybridomas assigned ATCC accession numbers PTA-9867, PTA-9868, PTA-9869, and PTA-9870 were received by the American Type Culture Collection (ATCC, Manassas, Va.) on Mar. 5, 2009 and deposited as of Apr. 3, 2009. Biological deposits of hybridomas assigned ATCC accession numbers PTA-9982, PTA-9983, PTA-9984, and PTA-9985 were received by the American Type Culture Collection (ATCC, Manassas, Va.) on Apr. 30, 2009 and deposited as of Jun. 4, 2009. In one preferred embodiment, for example, the monoclonal antibodies are 6E1, 6G12, 6F10, 1H9, 7F6, or a combination thereof. In another embodiment, the monoclonal antibody is 6E1.

It may be desirable to produce and use functional fragments of a monoclonal antibody for a particular application. The well-known basic structure of a typical IgG molecule is a symmetrical tetrameric Y-shaped molecule of approximately 150,000 to 200,000 daltons consisting of two identical light polypeptide chains (containing about 220 amino acids) and two identical heavy polypeptide chains (containing about 440 amino acids). Heavy chains are linked to one another through at least one disulfide bond. Each light chain is linked to a contiguous heavy chain by a disulfide linkage. An antigen-binding site or domain is located in each arm of the Y-shaped antibody molecule and is formed between the amino terminal regions of each pair of disulfide linked light and heavy chains. These amino terminal regions of the light and heavy chains consist of approximately their first 110 amino terminal amino acids and are known as the variable regions of the light and heavy chains. In addition, within the variable regions of the light and heavy chains there are hypervariable regions which contain stretches of amino acid sequences, known as complementarity determining regions (CDRs). CDRs are responsible for the antibody's specificity for one particular site on an antigen molecule called an epitope. Thus, the typical IgG molecule is divalent in that it can bind two antigen molecules because each antigen-binding site is able to bind the specific epitope of each antigen molecule. The carboxy terminal regions of light and heavy chains are similar or identical to those of other antibody molecules and are called constant regions. The amino acid sequence of the constant region of the heavy chains of a particular antibody defines what class of antibody it is, for example, IgG, IgD, IgE, IgA or IgM. Some classes of antibodies contain two or more identical antibodies associated with each other in multivalent antigen-binding arrangements.

Proteolytic cleavage of a typical IgG molecule with papain is known to produce two separate antigen binding fragments called Fab fragments which contain an intact light chain linked to an amino terminal portion of the contiguous heavy chain via by disulfide linkage. The remaining portion of the papain-digested immunoglobulin molecule is known as the Fc fragment and consists of the carboxy terminal portions of the antibody left intact and linked together via disulfide bonds. If an antibody is digested with pepsin, a fragment known as an F(ab')2 fragment is produced which lacks the Fc region but contains both antigen-binding domains held together by disulfide bonds between contiguous light and heavy chains (as Fab fragments) and also disulfide linkages between the remaining portions of the contiguous heavy chains (Handbook of Experimental Immunology. Vol 1: Immunochemistry, Weir, D. M., Editor, Blackwell Scientific Publications, Oxford (1986)).

Fab and F(ab')2 fragments of MAbs that bind thermostable bovine blood antigen can be used in place of whole MAbs in methods for detecting or quantifying thermostable bovine blood antigen in samples. Because Fab and F(ab')2 fragments are smaller than intact antibody molecules, more antigen-binding domains can be immobilized per unit area of a solid support than when whole antibody molecules are used. As explained below, rapid, easy, and reliable assay systems can be made in which antibodies or antibody fragment that specifically bind thermostable bovine blood antigen are immobilized on solid phase materials.

Recombinant DNA methods have been developed which permit the production and selection of recombinant immunoglobulin peptides which are single chain antigen-binding polypeptides known as single chain Fv fragments (ScFvs or ScFv antibodies). ScFvs bind a specific epitope of interest and can be produced using any of a variety of recombinant bacterial phage-based methods, for example as described in Lowman et al. (1991) Biochemistry, 30: 10832-10838; Clackson et al. (1991) Nature 352: 624-628; and Cwirla et al. (1990) Proc. Natl. Acad. Sci. USA 87: 6378-6382. These methods are usually based on producing genetically altered filamentous phage, such as recombinant M13 or fd phages, which display on the surface of the phage particle a recombinant fusion protein containing the antigen-binding ScFv antibody as the amino terminal region of the fusion protein and the minor phage coat protein g3p as the carboxy terminal region of the fusion protein. Such recombinant phages can be readily grown and isolated using well-known phage methods. Furthermore, the intact phage particles can usually be screened directly for the presence (display) of an antigen-binding ScFv on their surface without the necessity of isolating the ScFv away from the phage particle.

To produce an ScFv, standard reverse transcriptase protocols are used to first produce cDNA from mRNA isolated from a hybridoma that produces an MAb for bovine blood antigen. The cDNA molecules encoding the variable regions of the heavy and light chains of the MAb can then be amplified by standard polymerase chain reaction (PCR) methodology using a set of primers for mouse immunoglobulin heavy and light variable regions (Clackson (1991) Nature 352: 624-628). The amplified cDNAs encoding MAb heavy and light chain variable regions are then linked together with a linker oligonucleotide in order to generate a recombinant ScFv DNA molecule. The ScFv DNA is ligated into a filamentous phage plasmid designed to fuse the amplified cDNA sequences into the 5' region of the phage gene encoding the minor coat protein called g3p. *Escherichia coli* bacterial cells are than transformed with the recombinant phage plasmids, and filamentous phage grown and harvested. The desired recombinant phages display antigen-binding domains fused to the amino terminal region of the minor coat protein. Such "display phages" can then be passed over immobilized antigen, for example, using the method known as "panning", see Parmley and Smith (1989) Adv. Exp. Med. Biol. 251: 215-218; Cwirla et al. (1990) Proc. Natl. Acad. Sci. USA 87: 6378-6382, to adsorb those phage particles containing ScFv antibody proteins that are capable of binding antigen. The antigen-binding phage particles can then be amplified by standard phage infection methods, and the amplified recombinant phage population again selected for antigen-binding ability. Such successive rounds of selection for antigen-binding ability, followed by amplification, select for enhanced antigen-binding ability in the ScFvs displayed on recombinant phages. Selection for increased antigen-binding ability may be made by adjusting the conditions under which binding takes place to require a tighter binding activity. Another method to select for enhanced antigen-binding activity is to alter nucleotide sequences within the cDNA encoding the binding domain of the ScFv and subject recombinant phage populations to successive rounds of selection for antigen-binding activity and amplification (see Lowman et al. (1991) Biochemistry 30: 10832-10838; and Cwirla et al. (1990) Proc. Natl. Acad. Sci. USA 87: 6378-6382).

Once a ScFvis selected, the recombinant thermostable bovine blood antigen antibody can be produced in a free form using an appropriate vector in conjunction with E. coli strain HB2151. These bacteria actually secrete ScFv in a soluble form, free of phage components (Hoogenboom et al. (1991) Nucl. Acids Res. 19: 4133-4137). The purification of soluble ScFv from the HB2151 bacteria culture medium can be accomplished by affinity chromatography using antigen molecules immobilized on a solid support such as AFFIGEL™ (BioRad, Hercules, Calif.).

Other developments in the recombinant antibody technology demonstrate possibilities for further improvements such as increased avidity of binding by polymerization of ScFvs into dimers and tetramers (see Holliger et al. (1993) Proc. Natl. Acad. Sci. USA 90: 6444-6448).

Because ScFvs are even smaller molecules than Fab or F(ab')2 fragments, they can be used to attain even higher densities of antigen binding sites per unit of surface area when immobilized on a solid support material than possible using whole antibodies, F(ab')2, or Fab fragments. Furthermore, recombinant antibody technology offers a more stable genetic source of antibodies, as compared with hybridomas. Recombinant antibodies can also be produced more quickly and economically using standard bacterial phage production methods.

In one embodiment of the present invention, therefore, the immunoglobulin peptide is a monoclonal antibody fragment which retains the ability to bind antigens from bovine blood. In one embodiment, these fragments include Fab and Fab2 portions of 1B4, 1H9, 2B11, 3D6, 6E1, 6F10, 6G12 and 7F6. In another embodiment, Fab and Fab2 fragments are from 6E1, 1H9, 6G12, 6F10, and 7F6 antibodies. Such fragments are typically produced by proteolytic cleavage, such as papain or pepsin. Alternatively, antigen-binding fragments can be produced through the application of recombinant DNA technology or through synthetic chemistry.

Detection

Regardless of whether the assay is a direct or indirect method, a label (reporter molecule) is bound to a molecule having affinity for (i) the bovine blood antigen or (ii) an immunoglobulin peptide (the immunoglobulin peptide, in turn, having affinity for the bovine blood antigen). Thus, for example, the assay may comprise (i) a sandwich assay in which a capture immunoglobulin peptide is bound to the carrier, the capture immunoglobulin peptide binds bovine blood antigen in the sample, and the captured bovine blood antigen then binds a labeled immunoglobulin peptide, (ii) a direct assay in which sample is bound to the carrier and is exposed to labeled immunoglobulin peptide, or (iii) an indirect assay in which a capture immunoglobulin peptide is bound to the carrier, the capture immunoglobulin peptide binds bovine blood antigen in the sample, and any unbound capture immunoglobulin peptide then binds a labeled composition having affinity for the capture immunoglobulin peptide. For such uses, a wide range of labels and detection methods may be employed.

Detection methodology will depend upon the identity of the assayable tag on the binding agent, as commonly understood in the art. Kits for detection of tagged binding agents in the capture immunoassay described above are commercially available. Detection procedures include Western blots, enzyme-linked immunosorbent assays, radioimmunoassays, competition immunoassays, dual antibody sandwich assays, immunohistochemical staining assays, agglutination assays, and fluorescent immunoassays.

The assayable tag may be detectable directly or may bind to a reporter for which it has specificity. The assayable tag attached to the binding agent can be, for example, an enzyme, a coenzyme, an enzyme substrate, an enzyme co-factor, an enzyme inhibitor, a radionuclide, a chromogen, a fluorescer, a chemoluminescer, a free radical, or a dye. Alternatively, detection can be mediated by reporter reagents such as fluorescent avidins, streptavidins or other biotin-binding proteins or enzyme-conjugated streptavidins plus a fluorogenic, chromogenic, or chemiluminescent substrate.

In one embodiment, the tag is biotin, which is then recognized by avidin or streptavidin conjugated to a reporter, such as the enzyme horseradish peroxidase. For example, the tagged binding agent can be biotinylated ASF or biotinylated isolectin B4 from Vicia villosa lectin (VVLB4). Biotin is typically conjugated to proteins via primary amines (i.e., lysines). Usually, between three and six biotin molecules are conjugated to each binding agent molecule. The avidin homolog streptavidin, which is secreted by Streptomyces avidinii, is preferred as a linking agent because of its particularly high affinity for biotin.

A number offluorescent compounds such as fluorescein isothiocyanate, europium, lucifer yellow, rhodamine B isothiocyanate (Wood (1991) In: Principles and Practice of Immunoassay, Stockton Press, New York, pp. 365-392) can be used to label binding agents. In conjunction with the known techniques for separation of antibody-antigen complexes, these fluorophores can be used to quantify thermostable bovine blood antigen in samples. The same applies to chemiluminescent immunoassay in which case either thermostable bovine blood antigen antibody can be labeled with isoluminol or acridinium esters (Krodel (1991) In: Bioluminescence and Chemiluminescence: Current Status. John Wiley and Sons Inc. New York, pp 107-110; Weeks (1983) Clin. Chem. 29:1480-1483). Radioimmunoassay (Kashyap, M. L. et al., J. Clin. Invest. 60:171-180 (1977)) is another technique in which thermostable bovine blood antigen antibodies can be used after coupling with a radioactive isotope such as $^{125}$I. Some of these immunoassays can be easily automated by the use of appropriate instruments such as the IMX™ (Abbott, Irving, Tex.) for a fluorescent immunoassay and Ciba Corning ACS 180™ (Ciba Corning, Medfield, Mass.) for a chemiluminescent immunoassay. Kits for detection of tagged binding agents in ELISA procedures are commercially available.

In one embodiment, a streptavidin/peroxidase complex is used to assay the amount of biotin tag. The activity of the peroxidase enzyme linked to the streptavidin can then be detected through the addition of a peroxidase substrate. An example of a peroxidase substrate is 2,2'-Azino-bis(3-ethyl benzthiazoline-6-sulfonic acid) (ABTS).

Solutions with known amounts of bovine blood antigen can be used in the generation of standard curves.

In some embodiments, non-radioactive labels are attached by indirect means. In some embodiments, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. Any ligands and anti-ligands that will function can be used. In some embodiments in which the ligand has a natural antiligand, for example, biotin, thyroxine, and cortisol, it is used in conjunction with the labeled, naturally occurring anti-ligands. Alternatively, any haptenic or antigenic compound can be used in combination with an antibody.

In some embodiments, the immunoglobulin peptides are conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol.

As previously noted, detection of labels may occur by a range of methods. Examples of known methods include, but are not limited to immunoblotting, western blot analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. Any means may be used to detect labels. Thus, for example, where the label is a radioactive label, examples of means for detection include a scintillation counter or photographic film as in autoradiography. Where the label is a fluorescent label, it may be detected, for example, by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels are detected, for example, by providing appropriate substrates for the enzyme and detecting the resulting reaction product. Finally, simple colorimetric labels may be detected, for example, by observing the color associated with the label. Thus, in various dipstick assays, conjugated gold often appears dark purple, while various conjugated beads appear the color of the bead.

In another aspect, the present invention provides a method for detecting bovine blood in a food sample or an animal feed sample. The method comprises the steps of coating a solid surface with a first monoclonal antibody selected from the group consisting of 1B4, 1H9, 2B11, 3D6, 6E1, 6F10, 6G12 and 7F6; contacting the first monoclonal antibody with the food sample or the animal feed sample; contacting the food sample or the animal feed sample with a second monoclonal antibody selected from the group consisting of 1B4, 1H9, 2B11, 3D6, 6E1, 6F10, 6G12 and 7F6, wherein the second monoclonal antibody is different from the first monoclonal antibody and is conjugated to a detectable marker; and obtaining a detectable signal generated by said marker. This method can be performed by, for example, a sandwich immunoassay.

The present invention also provides an alternative method for detecting the presence of bovine blood in a food sample or an animal feed sample, wherein the method comprises coating a solid surface with the food sample or the animal feed sample; contacting the food sample or the animal feed sample with a monoclonal antibody selected from the group consisting of 1B4, 1H9, 2B11, 3D6, 6E1, 6F10, 6G12 and 7F6; contacting the monoclonal antibody with a detection antibody capable of binding said monoclonal antibody, wherein the detection antibody is conjugated to a detectable marker; and obtaining a detectable signal generated by said detectable marker. This method can be performed, for example, by non-competitive indirect ELISA.

The sandwich ELISA is used to determine the antigen concentration in unknown samples. For purposes of the present invention, the sample is a food sample or an animal feed sample. In one embodiment, a food sample is selected from meats. In another embodiment, a food sample is selected from ground meats. In another embodiment, the food sample is selected from butter and cheeses. In another embodiment, the food sample is selected from breads, cakes, crackers and other bakery products. In yet another embodiment, a food sample is selected from wines. An animal feed sample is selected from, for example, meat, bone meal, and protein enriched fodder containing bovine components, such as for example, spray dried bovine blood or plasma, or meat and bone meal components. In one embodiment, the animal feed sample is selected from meat and bone meal. In still another embodiment, the animal feed sample is fodder enriched with meat and bone meal or a bovine component.

The preparation of a food sample and an animal feed sample is the same for purposes of ELISA. Briefly, a food sample or an animal feed sample is cooked or autoclaved, e.g., by heating in a boiling water bath for about 15 minutes or by autoclaving, for example, for 15 minutes at 121° C. at 1.2 bars. Next, the cooked and autoclaved samples are mashed into fine particles and the extraction buffer is added. The samples are then homogenized and centrifuged, and the supernatants are used for ELISA, following determination of protein concentration. A complete protocol for preparing food or animal feed samples is described in Example 2.

The sandwich ELISA is fast and accurate, and if a purified antigen standard is available, the assay can determine the absolute amount of antigen in an unknown sample. The sandwich ELISA requires two antibodies that bind to epitopes that do not overlap on the antigen. This can be accomplished with either two monoclonal antibodies that recognize discrete sites or one batch of affinity-purified polyclonal antibodies. In one embodiment, the two monoclonal antibodies used in the ELISA are selected from the group consisting of 1B4, 1H9, 2B11, 3D6, 6E1, 6F10, 6G12 and 7F6. In another embodiment, the pair of monoclonal antibodies is 3D6 and 7F6. In another embodiment, the pair of monoclonal antibodies is 1B4 and 6F10. In another embodiment, the pair of monoclonal antibodies is 6G12 and 7F6. Additional antibody combinations can be determined based on antibody specificities as shown in Table 2. With respect to the labeling of a monoclonal antibody for purposes of signal detection, any label discussed above can be used. In one embodiment, the label is selected from biotin, horseradish peroxidase, fluorescein isothiocyanate, gold, and rhodamine B isothiocyanate.

To utilize this assay, one antibody (the "capture" antibody) is purified and bound to a solid phase typically attached to the bottom of a plate well. Antigen is then added and allowed to complex with the bound antibody. Unbound products are then removed with a wash, and a labeled second antibody (the "detection" antibody) is allowed to bind to the antigen, thus completing the "sandwich." The assay is then quantitated by measuring the amount of labeled second antibody bound to the matrix through the use of a colorimetric substrate. Major advantages of this technique are that the antigen does not need to be purified prior to use and that these assays are very specific. However, one disadvantage is that not all antibodies can be used. Monoclonal antibody combinations must be qualified as "matched pairs," meaning that they can recognize separate epitopes on the antigen so they do not hinder each other's binding.

A general protocol for the sandwich ELISA method is described below. Before the assay, both antibody preparations should be purified and one must be labeled. For most applications, a polyvinylchloride (PVC) microtiter plate is used. The unlabeled antibody is bound to the bottom of each well by adding approximately 50 μL of antibody solution to each well (e.g. 20 μg/mL in PBS). The amount of antibody used will depend on the individual assay. The plate is incubated overnight at 4° C. to allow complete binding. Next, the wells are washed, for example, two time, with PBS. The remaining sites for protein binding on the microtiter plate must be saturated by incubating with blocking buffer. This is generally done by filling the wells to the top with 1% BSA/PBS with 0.02% sodium azide, following which the plate is incubated for 2 hours to overnight in a humid atmosphere at room temperature. It is of note that sodium azide is not included in buffers or wash solutions if an HRP-labeled antibody will be used for detection. The wells are then washed, for example, two times, with PBS.

The antigen solution (generally 50 μL) is added to the wells. The antigen solution should generally be titrated. All dilutions should be done in the blocking buffer (1% BSA/PBS), and the plate is generally incubated for at least about 2 hours at room temperature in a humid atmosphere.

The plate is again washed with PBS, and the labeled second antibody is added. For accurate quantification, the second antibody generally is used in excess. All dilutions should be done in the blocking buffer. The plate is again incubated for about 1-2 hours or more at room temperature in a humid atmosphere and washed with several changes of PBS. The substrate is next added, and after the appropriate incubation time has elapsed, optical densities at target wavelengths can be measured on an ELISA plate reader.

In an alternative embodiment, when two "matched pair" antibodies are not available, another option is the competitive ELISA. Because of the probability for steric hindrance occurring when two antibodies attempt to bind to a small molecule at the same time, a competitive inhibition assay can be used in such a case. An advantage to the competitive ELISA is that non-purified primary antibodies may be used. There are several different configurations for competitive ELISAs, which are known to one of ordinary skill in the art. Below is an example for one such configuration.

In order to utilize a competitive ELISA, one reagent must be conjugated to a detection label, such as horseradish peroxidase. This enzyme may be linked to either the immunogen or the primary antibody. The protocol below uses a labeled immunogen as the competitor.

Briefly, an unlabeled purified primary antibody is coated onto the wells of a 96 well microtiter plate. This primary antibody is then incubated with unlabeled standards and unknowns. After this reaction is allowed to go to equilibrium, conjugated immunogen is added. This conjugate will bind to the primary antibody wherever its binding sites are not already occupied by unlabeled immunogen. Thus, the more immunogen in the sample or standard, the lower the amount of conjugated immunogen bound. The plate is then developed with substrate and color change is measured.

In another embodiment, a competitive ELISA is performed by coating the plate with immunogen, such as autoclaved bovine blood, adding an enzyme-conjugated monoclonal antibody selected from 1B4, 1H9, 2B11, 3D6, 6E1, 6F10, 6G12 and 7F6 together with an unknown sample, wherein the antigen in the unknown sample competes with the immobilized immunogen, and developing the plate.

An exemplary protocol for a competitive ELISA method is described below.

A diluted primary antibody (capture) is added to each well (generally 50 μL). The appropriate dilution should generally be determined prior to testing samples. The plate is then incubated for 4 hours at room temperature or 4° C. overnight. If a purified capture antibody is not available, the plate should generally first be coated with a purified secondary antibody directed against the host of the capture antibody according to the following procedure:

The unlabeled secondary antibody may be bound to the bottom of each well (e.g., by adding approximately 50 μL of antibody solution to each well). The plate is incubated overnight at 4° C., and the primary capture antibody is added.

The wells are then washed with PBS (e.g., twice). Next, the wells are incubated with 1% BSA/PBS with 0.02% sodium azide, and incubated for 1-2 hours to overnight in a humid atmosphere at room temperature, following which they are washed with PBS. The standards and sample solutions are added to the wells, wherein all dilutions are generally done in the blocking buffer (1% BSA/PBS with 0.05% Tween-20). Sodium azide should generally not be used in buffers or wash solutions, if an HRP-labeled conjugate is used for detection.

The antigen-conjugate solution (e.g., 50 μL) is added to the wells (the antigen solution should generally be titrated) and incubated for at least 2 hours at room temperature in a humid atmosphere, following which the plate is washed (e.g., four times) with PBS.

The substrate is next added to the plate, incubated for an appropriate amount of time, and optical densities at target wavelengths are measured on an ELISA reader. It is of note that competitive ELISAs yield an inverse curve, where higher values of antigen in the samples or standards yield a lower amount of color change.

In a sequential competitive inhibition assay, the sample and conjugated analyte are added in steps like a sandwich assay, while in a classic competitive inhibition assay, these reagents are incubated together at the same time.

In a sequential competitive inhibition assay format, a monoclonal antibody is coated onto a 96-well microtiter plate. When the sample is added, the monoclonal captures free analyte out of the sample. In the next step, a known amount of analyte labeled with either biotin or HRP is added. The labeled analyte will then also attempt to bind to the MAb adsorbed onto the plate; however, the labeled analyte is inhibited from binding to the MAb by the presence of previously bound analyte from the sample. This means that the labeled analyte will not be bound by the monoclonal on the plate if the monoclonal has already bound unlabeled analyte from the sample.

The amount of unlabeled analyte in the sample is inversely proportional to the signal generated by the labeled analyte. The lower the signal, the more unlabeled analyte there is in the sample. A standard curve can be constructed using serial dilutions of an unlabeled analyte standard. Subsequent sample values can then be read off the standard curve as is done in the sandwich ELISA formats.

Both sandwich ELISA and competitive ELISA are frequently used in the art, and a skilled artisan can readily modify the above described protocols.

Kits

The capture agent(s), labeled binding agent(s), revealing reagents, and/or standards for the conduct of the various capture immunoassays described herein may conveniently be supplied as kits which include the necessary components and instructions for performing the assay. Screening/diagnostic kits typically comprise one or more reagents that specifically bind to the target that is to be screened (e.g., ligands that specifically bind to thermostable bovine blood antigens). The reagents can, optionally, be provided with an attached label and/or affixed to a substrate (e.g. as a component of a protein array), and/or can be provided in solution. The kits can comprise nucleic acid constructs (e.g., vectors) that encode one or more such ligands to facilitate recombinant expression of such. The kits can optionally include one or more buffers, detectable labels or labeled binding agents, or other reagents as may be useful in a particular assay.

In addition, the kits optionally include labeling and/or instructional materials providing directions (i.e., protocols) for the practice of the methods described herein. Preferred instructional materials describe the detection of thermostable bovine blood antigen in animal feed or other samples. While the instructional materials typically comprise written or printed materials, they are not limited to such. Any medium capable of storing such instructions and communicating them to an end user is contemplated. Such media include, but are not limited to electronic storage media (e.g., magnetic discs, tapes, cartridges, chips), optical media (e.g., CD ROM), and the like. Such media may include addresses to internet sites that provide such instructional materials.

A preferred kit includes a microtiter plate coated with a thermostable bovine blood antigen immunoglobulin peptide capture agent, standard solutions for preparation of standard curve, a control for quality testing of the analytical run, thermostable bovine blood antigen conjugated to biotin, streptavidin-peroxidase enzyme, a substrate solution, a stopping solution, a washing buffer, and an instruction manual.

In some embodiments, the antibody is collectively assembled in a kit with conventional immunoassay reagents for detection of bovine blood. The kit may optionally contain a standard for the determination of the presence of bovine blood in a sample. The kit containing these reagents provides for simple, rapid, on site detection of bovine blood in a food sample or an animal feed sample.

For purposes of the kit, the monoclonal antibodies can be coated onto a solid phase, such as an ELISA microliter plate, later flow strips, a dipstick, magnetic beads, and the like, and used as a sensitive reagent to accurately detect bovine blood. This commercial kit form is useful for rapid and convenient use by regulatory agencies and the meat industry. The kit can be formulated to contain antibodies for a non-competitive ELISA, including double-sandwich ELISA assays and indirect ELISA, as well as competitive assays. However, other formats such as homogenous enzyme immunoassays may be developed. In one embodiment, the kit for performing sandwich ELISA contains the antibodies 3D6 and 6g12. In another embodiment, the kit for performing a competitive ELISA contains at least one of the antibodies 1B4, 1H9, 2B11, 3D6, 6E1, 6F10, 6G12 and 7F6. In another embodiment, the kit for performing a competitive ELISA contains at least one of 6E1, 6F10, 7F6 or 1H9.

In some embodiments, at least one monoclonal antibody that is used in a kit is labeled. A wide variety of labels and conjugation techniques are known and are reported extensively in both the scientific and patent literature. In some embodiments, the antibody is labeled indirectly by reaction with labeled substances that have an affinity for the antibody, such as protein A or G. Any label, detectable group, conjugation technique or other method of labeling may be used. Suitable labels include radioactive molecules, enzymes, substrates, cofactors, inhibitors, fluorescent moieties, chemiluminescent moieties, magnetic particles, and the like. The detectable group can be any material having a detectable physical or chemical property. Such detectable labels have been well-developed and, in general, any label useful in such methods can be applied to the present method. Thus, a label is any composition detectable by spectroscopic, photochemical, biochemical, immunochemical, electrical, optical, chemical, or any other means. Useful labels in the present invention include fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., LacZ, CAT, horst radish peroxidase, alkaline phosphatase and others, commonly used as detectable enzymes, either in an EIA or in an ELISA), and colorimetric labels such as colloidal gold or colored glass or plastic (e.g. polystyrene, polypropylene, latex, etc.) beads. The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Other features, objects and advantages of the present invention will be apparent to those skilled in the art. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the present invention.

All publications and patent applications cited in this specification are herein incorporated by reference as if each individual publication or patent application was specifically and individually indicated to be incorporated by reference.

DEFINITIONS AND ABBREVIATIONS

The term "animal byproduct" as used herein means one or more of those parts or portions of animals that are typically discarded during the processing of animals for the preparation of meat products from animals for human consumption. Examples include, but are not limited to bone, connective tissue (e.g., cartilage, tendons, ligaments, and fascia), skin, hair, feathers, beaks, hooves, horns, claws, fat, greaves, blood, certain muscles, and combinations thereof.

The term "antigen" refers to a foreign substance that, when introduced into the body, can stimulate an immune response.

The term "analyte," refers to a substance to be detected which may be present in the test sample. The analyte can be any substance for which there exists a naturally occurring specific binding member (such as an antibody), or for which a specific binding member can be prepared.

The term "animal feed" includes any food stuff that is used to feed livestock, such as cattle, sheep, goats, pigs, chickens, turkey, ducks, etc.

The term "epitope" means an antigenic determinant of a polypeptide or protein.

The terms "Fab" and "Fab2" refer to antibody fragments obtained by digestion with papain and pepsin, respectively. Fab contains a single antigen binding site, whereas Fab2 contains two antigen-binding sites. Fab and Fab2 also include such fragments which are produced by recombinant DNA technology or synthetic chemistry.

The term "monoclonal antibody" refers to a single type of antibody that is directed against a specific epitope (antigenic determinant) and is produced by a single clone of B cells or a single hybridoma cell line. "MAb" is an abbreviation for monoclonal antibody.

The term "polyclonal antibody" refers to a mixture of antibodies active against a specific antigen, each recognizing a different epitope or region of the antigen.

The term "rendered" as used herein, is defined to have its broadest possible meaning to include all types of rendering processes in the animal meat processing and packaging industry, including processes that include a step of physically milling, grounding, or otherwise processing into particles of small size and heating. The purpose of heating may be, for example, to kill pathogens, to render the material more digestible, to separate fat from non-fat materials, or all of the them. One non-limiting example of a rendering temperature is between approximately 121° and approximately 138° C., although heating temperatures vary depending on whether the heating is performed under pressure as well as the duration of heating.

The term "rendered animal byproduct" as used herein shall mean animal byproduct that has been rendered.

The term "meat and bone meal" (or "MBM") as used herein refers to a type of rendered animal byproduct. MBM is made by rendering animal byproducts of the meat packing industry. Examples of commercial providers of MBM include, but are not limited to, ConAgra Foods, (Greeley Colo.), Darling International (Irving, Tex.); Excel Corporation (Wichita, Kans.); National By-Products, (Des Moines, Iowa); and Valley Proteins, Inc., (Winchester, Va.).

Having described the invention in detail, it will be apparent that modifications and variations are possible without departing the scope of the invention defined in the appended claims. Furthermore, it should be appreciated that all examples in the present disclosure, while illustrating the invention, are provided as non-limiting examples and are, therefore, not to be taken as limiting the various aspects of the invention so illustrated.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Production of Monoclonal Antibodies Specific to Bovine Blood Thermal Stable Proteins Extraction of Thermal-Stable Soluble Protiens (TSPs) from Whole Animal Blood Soluble TSPs were extracted from cooked and autoclaved whole blood sample from each species (bovine, porcine, ovine, equine, rabbit, turkey and chicken). Twenty mL of each blood sample was dispensed into a 50-ml beaker to prepare the "autoclaved blood sample." The beaker was covered with aluminum foil and autoclaved for 15 minutes at 121° C. at 1.2 bars. Another beaker containing 20 mL of blood sample from each species was heated in a boiling water bath for 15 minutes to obtain "cooked blood sample." Both autoclaved and cooked blood samples from each species were then mashed into fine particles using a glass rod. An equal volume (20 mL) of the extraction buffer (10 mM phosphate buffered saline) was added to the mashed samples to extract the soluble TSPs and the mixture was homogenized for 2 minutes at 11000 RPM using the ULTRA-TURRAX T25 basic homogenizer (IKA Works Inc., Wilmington, N.C.). The homogenized samples were covered with paraffin films and allowed to stand for 2 hours at room temperature followed by another 2 hours at 4° C. The mixtures were then transferred into centrifuge tubes and centrifuged (Eppendorf 5810R centrifuge, Brinkman Instruments Inc., Westbury, N.Y.) at 3220×g for 60 minutes at 4° C. The supernatants of cooked and autoclaved blood samples were then filtered through Whatman No. 1 filter paper. The protein concentration of clear filtrates was determined by protein assay kit II (Bio-Rad, Hercules, Calif.) based on the Bradford dye-binding method. Bovine serum albumin (BSA) was used as the standard in this assay. All protein extracts were stored at −20° C. until use.

Production of monoclonal Antibodies Specific to bovine TSPs Immunization

The autoclaved bovine blood TSP crude extract was dialyzed in 10 mM PBS for 24 hours and the dialyzed extract was used as the immunogen. This partially purified crude protein extract was used to immunize animals because all individual TSP in the extract could be a potential antigen to elicit antibody production. Three female BALB/c mice were immunized subcutaneously with 100 µg/mouse of the dialyzed TSPs in phosphate buffered saline (PBS) emulsified with an equal volume of Freund's complete adjuvant. Several boost injections prepared in the same manner using Freund's incomplete adjuvant were applied to each mouse at 4-week intervals. Test sera from mice were collected 8 days after each boosting by tail bleeding. The titer of the sera was determined by indirect ELISA. The mouse showing the highest titer was injected intraperitoneally with 100 µg of marker protein in PBS 4 days prior to fusion.

Hybridoma Procedures

The spleen cells from the immunized mouse were fused with murine myeloma cells (P3x63.Ag8.653, ATCC CRL 1580) for hybridoma production. The general procedures as described by Kohler and Milstein (1975) were followed with modifications and the following specific screening procedures. Those hybridomas secreting antibodies that react with the target antigen were selected, cloned twice by limiting dilution, and expanded. The initial screening against the antigen (autoclaved bovine TSPs) was performed using indirect ELISA. For a secondary selection, the positive cells from the initial screening were expanded and the supernatants were screened for reactivity with the native blood serum proteins, TSPs from the cooked blood samples from bovine and other animal species; and various bovine tissue protein extracts. Hybridomas with distinct reaction patterns to bovine target TSPs were selected. Monoclonal antibodies (MAbs) showing positive reaction to antigens will include both IgM and IgG classes. Because IgM antibodies are generally more difficult to purify and store, only IgG class of MAbs were selected. This can be achieved by using IgG γ-chain specific secondary antibody as a probe in the ELISA screening procedures.

MAbs were obtained in supernatants from propagated cell cultures and in ascites fluid from mice injected with hybridoma cells. The isotype of the selected MAb was determined with a mouse MAb isotyping kit (Sigma) according to the manufacturer's protocol. MAb IgGs were purified using a Bio-Rad Protein A Cartridge with the Bio-Rad Econo LC system. The concentration of IgG in the final preparation was determined by UV absorption at 280 nm. The purified MAbs were titrated against the antigen by indirect ELISA to confirm the immunoreactivity. The antigenic components for each MAb were determined by Western blotting.

Characterization of Monoclonal Antibodies (MAbs) Indirect Enzyme-Linked Immunosorbent Assay (ELISA)

One hundred microliter (100 μL) of each sample protein extract and controls properly diluted in 0.06M carbonate buffer (pH 9.6) such that each 100 μL contained 0.5 μg of soluble protein, was coated unto the wells of a 96-well polyvinyl microplate and incubated at 37° C. for 2 hours. The plate was then washed 3 times with PBST [0.05% v/v Tween-20 in 1 mM PBS, pH 7.2] and incubated with 200 μL/well blocking solution (1% BSA in PBS) at 37° C. for 2 h followed by another washing step. The undiluted primary MAb supernatants (100 μL) or appropriately diluted in antibody buffer [1% w/v BSA in PBST] was added to each well and incubated at 37° C. for 2 hours. After washing 3 times with PBST, diluted (1:3,000 in antibody buffer) horseradish peroxidase-conjugated goat anti-mouse IgG-Fc specific solution was added. The plate was incubated at 37° C. for 3 h and then washed 5 times before the addition of the substrate solution (22 mg of 2,2'-azino-di-[3-ethyl-benothiazoline-6-sulfonic acid] and 15 μL of 30% hydrogen peroxide in 100 ml of 0.1 M phosphate-citrate buffer, pH 4.0). Color was developed at 37° C. for 20 min and the enzyme reaction was stopped by adding 0.2 M citric acid solution (42 g citric acid monohydrate dissolved in 1000 mL deionized water). Absorbance was measured by a microplate reader (Bio-Rad, Model 450) at 415 nm. This technique was used to test titers of the antisera, screen hybridoma clones, produce saturation curves for each MAb, test for specificity of MAbs, and verify the cross reactivity of each MAb.

Table 1 summarizes the distinctive species-specific immunoreactivities of monoclonal antibodies to proteins extracted from heat-treated (cooked at 100° C. for 15 min or autoclaved at 121° C., 15 min, 1.2 bars) and non-treated whole blood of different animal species (horse, pig, sheep, cattle, chicken, turkey and rabbit), and their cross-reactivity with several non-blood proteins (meat proteins, bovine serum albumin, gelatin and non-fat dry milk proteins) using indirect ELISA. All MAbs were developed by immunizing animals with thermal-stable crude soluble protein/peptide mixtures extracted from autoclaved bovine whole blood with 10 mM PBS as described in greater detail herein.

TABLE 1

Characterization of Monoclonal Antibodies

| MAb (Subclass) | Species Specificity | | | Cross reactivity |
|---|---|---|---|---|
| | Autoclaved samples | Cooked Samples | Raw samples | With non-blood proteins |
| 1B4 (IgG1) | Equine ++++ Porcine ++++ Ovine ++++ Bovine ++++ | Equine +++ Porcine +++ Ovine ++++ Bovine ++++ | Equine +++ Porcine ++ Ovine ++ Bovine ++ | – |
| 1H9 (IgG1) | Bovine ++++ Ovine +++ | Bovine ++++ Ovine ++++ | Bovine ++++ Ovine ++++ | – |
| 2B11 (IgG1) | Bovine ++++ Rabbit ++++ | Bovine ++ Rabbit ++ | Bovine ++ Rabbit + | BSA ++++ |
| 3D6 (IgG1) | Bovine +++ Equine ++++ | Bovine +++ Equine ++++ | Bovine + | – |
| 6E1 (IgG1) | Bovine ++++ | Bovine ++++ | Bovine + | – |
| 6F10 (IgG1) | Bovine ++++ Ovine +++ | Bovine ++ Ovine ++ | Bovine + | – |
| 6G12 (IgG1) | Bovine ++ Ovine ++++ | Bovine ++ Ovine ++++ | Bovine + | – |
| 7F6 (IgG1) | Bovine ++ Ovine ++++ | Bovine ++ Ovine ++++ | Bovine + | – |

+ = weak reaction,
++ = moderate reaction,
+++ = strong reaction,
++++ = very strong reaction,
– = negative reaction

Sodium Dodecyl Sulfate-Polyacrylamide Gel Electrophoresis (SDS-PAGE)

SDS-PAGE was performed to resolve the soluble TSPs of different blood sample extracts. Western blot was then carried out to transfer proteins from the gel to nitrocellulose membrane in order to determine the molecular weights of the immunogenic components which reacted with developed MAbs. The general procedures of SDS-PAGE were performed according to the method of Laemmli (1970) with modifications. Briefly, soluble proteins from the samples were separated on 5% stacking gel (pH 6.8) and a 12% polyacrylamide separating gel (pH 8.8). The gel was electrophoresed at 200 V for 45 minutes using a Mini-Protein 3 electrophoresis cell (Bio-Rad, 161-3301) with 1× Tris/Glycine/SDS buffer (100 mL 1× Tris/Glycine/SDS buffer in 900 mL DDI water, pH 8.3) connected to a power supply (Bio-Rad Model 3000). Samples were diluted such that there was 3 μg of protein per each 15 μL of sample loaded into the well.

Table 2 summarizes the antigenic components in the blood protein extracts probed by each monoclonal antibody produced using Western blot.

TABLE 2

Antigenic Components in the Blood Protein Probed by Certain MAbs

| | Laboratory prepared blood extracts & commercial plasma samples | | | | | | | Estimated |
|---|---|---|---|---|---|---|---|---|
| Mab | Bba | Sba | Rba | Hba | Pba | Bbm | Bpm | MW |
| 1B4 | ++++ | ++++ | – | ++++ | ++++ | ++ | ++ | 25 kDa |
| 1H9 | +++ | ++ | – | – | – | ++ | +++ | 10 kDa |
| 2B11 | ++ | – | ++ | – | – | – | ++ | 10 kDa |
| 3D6 | ++++ | – | – | ++++ | + | ++ | ++++ | 60 kDa |
| 6E1 | ++++ | – | – | – | – | ++++ | ++++ | 40 kDa |

TABLE 2-continued

Antigenic Components in the Blood Protein Probed by Certain MAbs

| Mab | Laboratory prepared blood extracts & commercial plasma samples | | | | | | | Estimated MW |
|---|---|---|---|---|---|---|---|---|
|  | Bba | Sba | Rba | Hba | Pba | Bbm | Bpm |  |
| 6F10 | ++ | +++ | − | − | − | − | − | 25 kDa |
| 6G12 | ++++ | ++++ | − | − | − | ++ | +++ | 60 kDa |
| 7F6 | ++++ | ++++ | − | − | − | ++ | +++ | 60 kDa |

Bba = autoclaved bovine blood,
Sba = autoclaved ovine blood,
Rba = autoclaved rabbit blood,
Hba = autoclaved equine blood,
Pba = autoclaved porcine blood,
Bbm = commercial bovine blood meal,
commercial Bpm = bovine plasma meal,
MW = molecular weight of antigenic protein/peptide components.
+ = weak antigenic band,
++ = moderate antigenic band,
+++ = strong antigenic band,
++++ = very strong antigenic band,
− = negative antigenic band.

Western Blot

Western blots were performed according to Towbin and Others (1979) with modifications. After separation of the proteins on 12% polyacrylamide gel by means of SDS-PAGE, protein bands were transferred electrophoretically (1 h at 100V) from the gel to nitrocellulose membranes using a MiniTrans-Blot unit (Bio-Rad) with 25 mM Tris, 192 mM glycine, and 20% (v/v) methanol buffer (pH 8.3). Upon completion of the transfer, the membrane was washed with TBST (20 mM Tris, 500 mM NaCl, 0.05% Tween-20, pH 7.5), blocked with 3% gelatin in PBS, and incubated with the undiluted MAb supernatant. The excess antibody was removed by washing with TBST, and the membrane was incubated with goat anti-mouse IgG-alkaline phosphatase conjugate diluted 1:3,000 in antibody buffer for 1 h at room temperature. After washing, the membrane was incubated with 5-bromo-4-chloro-3-indolyl phosphate/p-nitroblue tetrazolium chloride (BCIP/NBT) in 0.1 M Tris buffer, pH 9.5. The color development was observed within 10 to 20 min and reaction was stopped by washing the membrane with distilled water. The appearance of a dark purplish band indicated the antibody binding site. The prestained broad range protein standards (Precision Plus Protein Kaleidoscope Standards, Bio-Rad, 161-0375) were used as molecular weight markers in both SDS-PAGE and Western blot.

Example 2

Development of a Sandwich Elisa for the Detection of Bovine Blood in Animal Feedstuff and in Ground Beef Characterization of MAbs Specificity and Cross-Reactivity Species and tissues specificity of MAbs were determined by testing each MAb supernatant with raw, cooked and autoclaved blood extracts from different animal species, meat extracts, and extracts from other proteins using indirect ELISA procedures as described in Example I.

Epitope Comparison

Epitope comparison was performed to search two comparable MAbs for construction of a sandwich ELISA. The ELISA method developed by Friguet and others (1983) was adapted for comparison of the relative binding sites of MAbs on the antigen. This test is based on an estimation of the limited number of antigenic sites simultaneously available to a pair of MAbs. The binding of the first MAb on the antigen inhibits the binding of the second MAb if both bind to the same or relatively close epitopes. However, if a pair of MAbs recognizes different epitopes, then the reaction can be additive. The epitope comparisons between any two MAb combinations were performed in two stages, namely generation of saturation curve to estimate the amount of each antibody required to saturate the antigen coated on the wells followed by the additivity test using indirect ELISA procedures.

To generate saturation curves, 200 µL of autoclaved bovine blood diluted in carbonate buffer (pH 9.6) to correspond to a concentration of 0.5 µg protein per 100 µL of coated sample, was coated into the wells of a microplate and incubated for 2 hours at 37° C. After 3 washings, the plate was blocked with BSA and incubated at 37° C. for 2 hours. After 2 further washings, 200 µL serial dilutions of MAb supernatant or purified IgG in antibody buffer (1% w/v BSA-PBST), were added to the plate and the plate was incubated for 1 hour at 37° C. After washing 3 times, 100 µL of horseradish peroxidase conjugated goat anti-mouse IgG (Fc specific), diluted 1:3000 in antibody buffer was added to the plate and incubated for 1 hour at 37° C. The remaining color development procedures were the same as described in the indirect ELISA. A plot with absorbance on the y-axis and reciprocal of the antibody dilution on the x-axis was constructed to obtain the saturation curve. The dilution of the antibody required to saturate the coated antigen was obtained from the saturation curve for each antibody tested, as the point at which the curve remains level or starts to drop.

To perform the additivity test for the two antibodies tested), autoclaved bovine blood extract (0.5 µg in 100 µL) diluted in carbonate buffer (pH 9.6) was coated unto the wells of a microplate and incubated for 2 hours at 37° C. After 3 washings, the plate was, blocked with 200 µL BSA solution and incubated at 37° C. for 2 hours. After 2 further washings, 100 µL of the MAb #1 properly diluted in antibody buffer to saturate the coated antigen (as determined from the saturation curve), was introduced into one well of the microplate. Another 100 µL of the MAb #2 sufficiently diluted to saturate the coated antigen (as determined from the saturation curve) was dispensed into the second well of the microplate. One hundred microliter (100 µL) each of the first and second primary antibody at the same levels of dilution to saturate the coated antigen were then introduced together into the third well of the microplate. The plate was then incubated at 37° C. for 2 hours. The remaining procedures of the ELISA were the same as described previously. The absorbance was read at 415 nm for the MAb #1 alone ($A_1$), the MAb #2 alone ($A_2$) and the two MAbs together ($A_{1+2}$). The additivity index (A.I.) for the two MAbs was computed based on the formula below:

$$A.I. = \left[\frac{2A_{1+2}}{A_1 + A_2} - 1\right] \times 100$$

If the two MAbs bind randomly at the same epitope, $A_{1+2}$ should be equal to the mean value of $A_1$ and $A_2$ and A.I. will be equal to zero. If, on the contrary, the two MAbs bind independently at distinct sites on the antigen molecule, $A_{1+2}$ should be the sum of $A_1$ and $A_2$ and A.I. will be equal to 100%. Thus for this experiment, for A.I. values below 50%, the MAbs were considered to inhibit each other's binding to the antigen, therefore, incapable of being used for the construction of a Sandwich ELISA. For A.I. values between 50% and 100%, the antibodies were considered to bind to different epitopes on the antigen molecule and therefore capable of being used to construct a Sandwich ELISA. In this sample experiment, MAb 3D6 and MAb 6G12 were selected to demonstrate the sandwich ELISA development.

MAb Purification and Biotinylation

Ascites fluids of selected MAbs were purified with Protein A column (Bio-Rad, 732-0091) in accordance with the manufacturer's instructions using the Econo System (Bio-Rad, 731-8101). The purified IgG (e.g. MAb 3D6) was subjected to biotinylation by first dialyzing in 0.1M $NaHCO_3$ [16.802 g $NaHCO_3$ in 2 L deionized water with pH adjusted to 8.3] for 24 hours at 4° C. The dialyzing buffer (0.1M $NaHCO_3$) was changed four times within the period. The protein concentration of the dialyzed antibody was determined by determining the absorbance at 280 nm (the UV assay) using the SmartSpec 3000 spectrophotometer (Bio-Rad). Ten-milligram (10 mg) NHS-CA-Biotin (Biotinamidocaproic acid 3-sulfo-N-hydroxysuccinimide ester) was dissolved in 1 mL DMF (N,N-Dimethyl Formamide) and added to the dialyzed antibody such that to each mg of dialyzed antibody, 100 μg of NHS-CA-Biotin in DMF was added. The mixture was incubated at room temperature for 1 hour and dialyzed overnight in 1 mM PBS at 4° C. The protein concentration of the biotinylated antibody was determined by UV assay prior to storage at −20° C.

Sample Preparations

Preparation of Flesh (Meat) and Non-Flesh Protein Samples

COOKED AND AUTOCLAVED MEAT EXTRACTS—Fat and connective tissues were trimmed off meat samples (beef, pork, lamb, rabbit, horse, chicken, and turkey). The lean meat sample was then cut up and ground twice using a meat grinder (Waring consumer Products, East Windsor, N.J.) to ensure thoroughness and homogeneity. Ten-gram (10 g) of minced meat sample from each species was weighed into beakers. The beakers were covered with aluminum foil, sealed with adhesive tape and autoclaved for 15 minutes at 121° C. and a pressure of 1.2 bars. Another portion (10 g) of minced meat sample from each species was weighed into a beaker. The beaker was covered with aluminum foil and the heated in a boiling water bath for 15 minutes. The autoclaved and cooked samples were then mashed into fine particles using a glass rod. Ten-milliliter (10 mL) of extraction buffer (10 mM PBS) was then added to the mashed autoclaved and cooked samples to extract the soluble proteins. The mixture was then homogenized for 2 minutes at 11000 RPM. The homogenized sample was then kept at room temperature for 2 hours followed by another 2 hours at 4° C. The mixtures were transferred in to centrifuge tubes and centrifuged at 3220×g for 60 minutes at 4° C. The supernatant was then filtered through Whatman No. 1 filter paper. The clear filtrates were used as the autoclaved and cooked meat sample extracts for the sandwich ELISA.

RAW BEEF EXTRACT—Ten-gram (10 g) of minced raw beef was weighed into a sampling bag. Ten-milliliter (10 mL) of extraction buffer (10 mM PBS) was added to extract the soluble proteins. The mixture in the sampling bag was blended in a stomacher (Model Number STO 400, Tekmar Company, Cincinnati, Ohio) for 60 seconds and allowed to stand at room temperature for 2 hours followed by another 2 hours at 4° C. The mixture was transferred in to a centrifuge tube and centrifuged and filtered as described above. The clear filtrates were used as raw meat extract for the sandwich ELISA.

NON-FLESH PROTEINS—The non-flesh proteins used were gelatin, soy protein concentrate, egg albumin, nonfat dry milk, Dairy Blend and bovine serum albumin. To 2 g each of the non-flesh proteins in a beaker was added 10 mL of extraction buffer (10 mM PBS) to extract the soluble proteins. The mixtures in beakers were covered with parafilms and kept at 2 hours at room temperature followed by another 2 hours at 4° C. The mixtures were then transferred into centrifuge tubes and centrifuged at 3220×g for 60 minutes at 4° C. The supernatant was filtered through Whatman No. 1 filter paper and the clear filtrates were used in the sandwich ELISA.

Preparation of Commercial Feedstuffs

To 2 g each of bovine meat bone meal, sheep meat bone meal, porcine meat bone meal, feather meal, spray-dried bovine plasma, whole bovine blood powder, and spray-dried porcine plasma was added 10 mL of extraction buffer (10 mM PBS) to extract the soluble proteins. The mixtures were extracted, centrifuged and filtered as described above.

Preparation of Laboratory of Adulterated Feed and Ground Beef Samples

Artificially adulterated samples used in this experiment were 1) autoclaved bovine blood in autoclaved porcine blood; 2) spray-dried bovine plasma and whole bovine blood powder in spray-dried porcine plasma; and 3) bovine blood in raw and cooked ground beef.

Autoclaved bovine blood in autoclaved porcine blood adulterated samples were prepared by mixing autoclaved porcine blood extract with autoclaved bovine blood extract to give 0 to 10% (v/v) adulterated samples with 0% been autoclaved porcine blood with no added autoclaved bovine blood. Likewise, the spray-dried bovine plasma in spray-dried porcine plasma adulterated samples were prepared by mixing spray-dried porcine plasma extract with spray-dried bovine plasma extract to give a 0 to 10% (v/v) level of adulteration. Whole bovine blood powder in spray-dried porcine plasma adulterated samples were prepared by mixing spray-dried porcine plasma extract with whole bovine blood powder extract to give a 0 to 10% (v/v) level of adulteration.

Preparation of Laboratory Adulterated Ground Beef Samples

Cooked and raw ground beef adulterated with bovine blood, were prepared in two ways. In the first case, prepared cooked ground beef extract was mixed with cooked bovine blood extract to give a 0 to 10% v/v bovine blood in cooked ground beef, with 0% being cooked ground beef extract without added cooked bovine blood. Bovine blood in raw ground beef was prepared similarly by mixing raw ground beef extracts with raw bovine blood to give a 0 to 10% v/v spiked bovine blood in raw ground beef extracts, with 0% being raw ground beef without added raw bovine blood.

Alternatively, samples were prepared by mixing bovine whole blood with fresh ground beef at 0% to 50% (v/w) levels. Ten grams of ground beef was weighed into beakers, a volume of 100 µL, 300 µL, 500 µL, 1 mL, 2 mL, 3 mL, 4 mL and 5 mL of bovine blood was added to each beaker to give 1, 3, 5, 10, 20, 30, 40 and 50% v/w spiked bovine blood in ground beef samples, respectively. The blood and beef mixture was thoroughly mixed, covered with aluminum foil, and heated in boiling water bath for 15 minutes. After cooling, 10 ml of extraction buffer (10 mM PBS) was added and the mixture was homogenized for 2 minutes at 11000 RPM. The mixtures were covered with paraffin films and allowed to stand for 2 hrs at room temperature followed by another 2 hours at 4° C. The mixtures were centrifuged at 3220×g for 60 minutes at 4° C. The supernatant was filtered through Whatman No. 1 filter paper and the clear filtrate was used as cooked sample extract for that sandwich ELISA.

Adulterated blood in raw beef extracts were mixed the blood and ground beef in a similar fashion as the cooked samples. The mixtures were transferred into sampling bags and to this was added 10 mL of extraction buffer. The mixtures were then blended in a stomacher for 60 seconds and allowed to stand at room temperature for 2 hours followed by another 2 hours at 4° C. The mixtures were transferred into centrifuge tubes and centrifuged and filtered and the clear filtrate was used as the raw blood adulterated beef sample extracts for analysis.

Sandwich ELISA

The experimental conditions including incubation time, titers of antibodies, and sample dilution of the sandwich ELISA were optimized to achieve the highest sensitivity and detectability. One hundred microliter (100 µL) of the capture antibody (MAb 6G12 purified IgG) diluted 1:1000 in antibody buffer (1% BSA-PBST), which corresponds to 0.18 µg protein per 100 µL was coated on the wells of a microplate and incubated at 37° C. for 2 hours. The plate was washed three times with PBST and then incubated for 1 hour at 37° C. with 200 µL of blocking buffer (1% BSA-PBS). After washing the plate twice with PBST, 100 µL of controls and samples appropriately diluted in antibody buffer was added to the plate and the plate was incubated for 2 hours at 37° C. The plate was washed thrice and incubated with 100 µL of the detection antibody (biotin-conjugated 3D6) diluted 1:1000 (which corresponds to 0.175 µg protein per 100 µL) in antibody buffer for 2 hours at 37° C. After further washing three times, the plate was incubated for 1 hour at 37° C. with 100 µL of the enzyme, streptavidin peroxidase polymer. After another washing step for five times, 100 µL of the enzyme substrate (ABTS with added $H_2O_2$) was added to the wells and the color was developed for 20 minutes at 37° C. At the end of the 20 minutes, 100 µL of stop solution (0.2M citric acid solution) was added to stop the reaction. The absorbance was then read at 415 nm.

Validation of the Sandwich ELISA

The performance of the optimized sandwich ELISA using MAbs 3D6 as the capturing antibody and MAb 6G12 as the detecting antibody was evaluated and validated in term of the criteria including the limit of detection, intra-assay and inter-assay variability (reproducibility), sensitivity, specificity and overall accuracy.

Figure 8A:
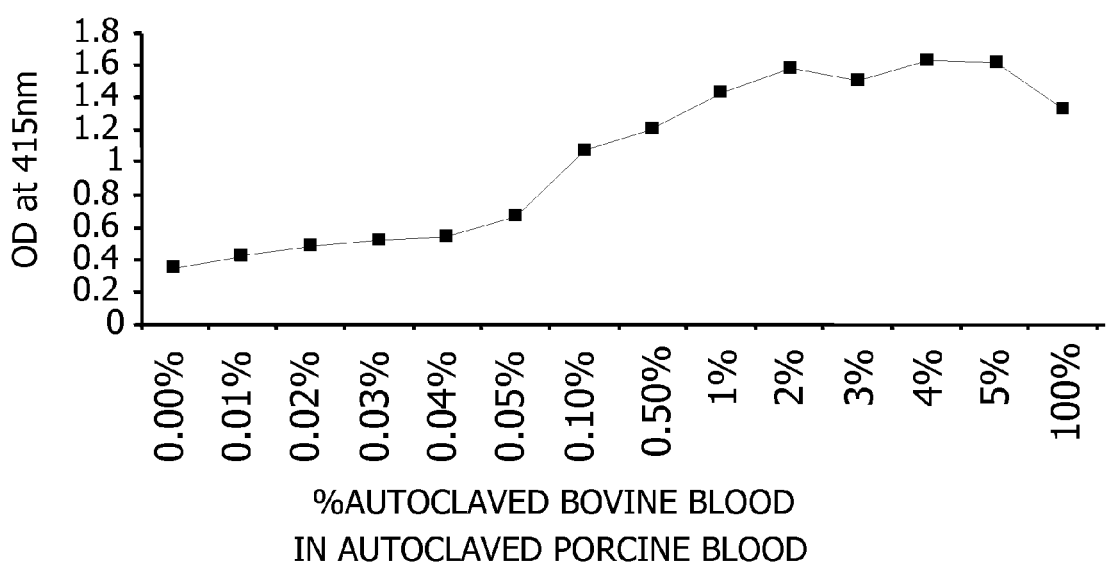
FIGS. 8A and 8B are graphs depicting the detection of autoclaved bovine blood in autoclaved porcine blood by antibodies 6G12 (capture antibody) and 3D6 (biotin conjugated detection antibody) when used in a sandwich ELISA as more fully described in Examples 2 and 3.
Figure 8B:
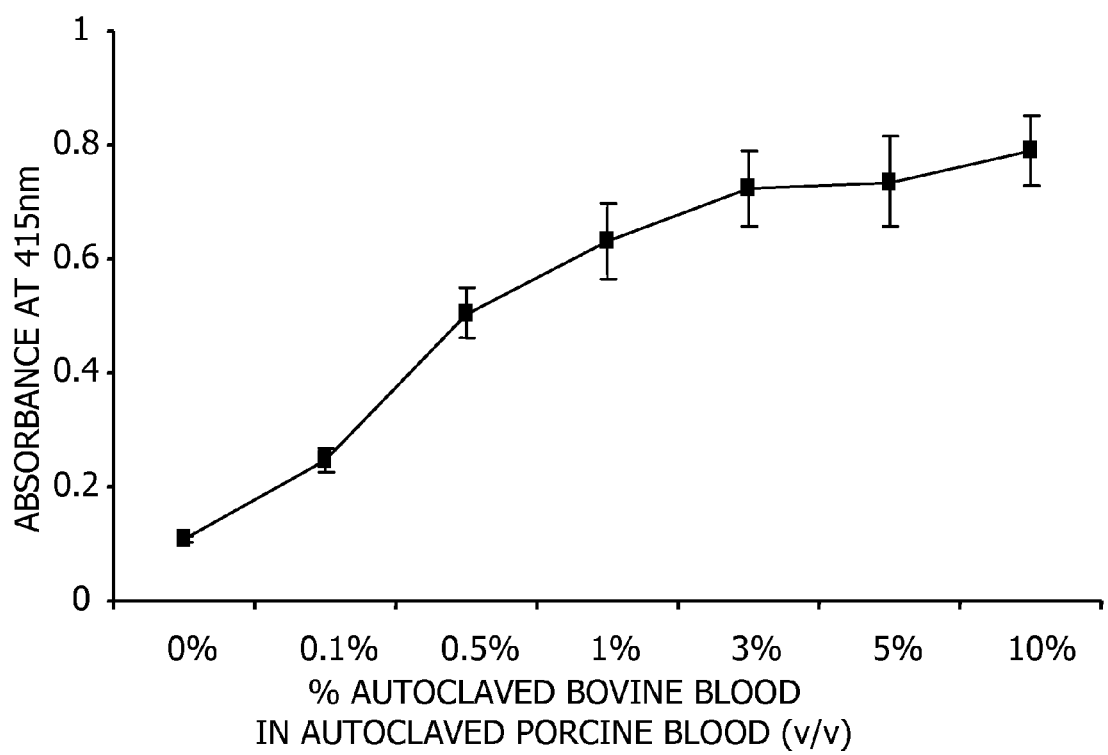
Figure 9:
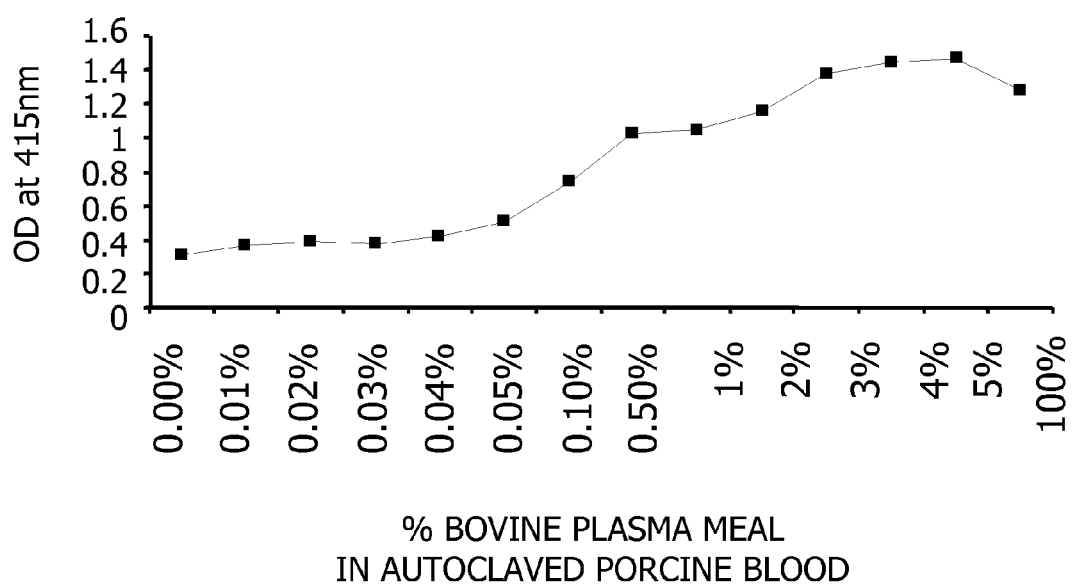
FIG. 9 is a graph depicting the detection of bovine plasma meal in autoclaved bovine blood by antibodies 6G12 (capture antibody) and 3D6 (biotin conjugated detection antibody) when used in a sandwich ELISA as more fully described in Examples 2 and 3.
Figure 10:
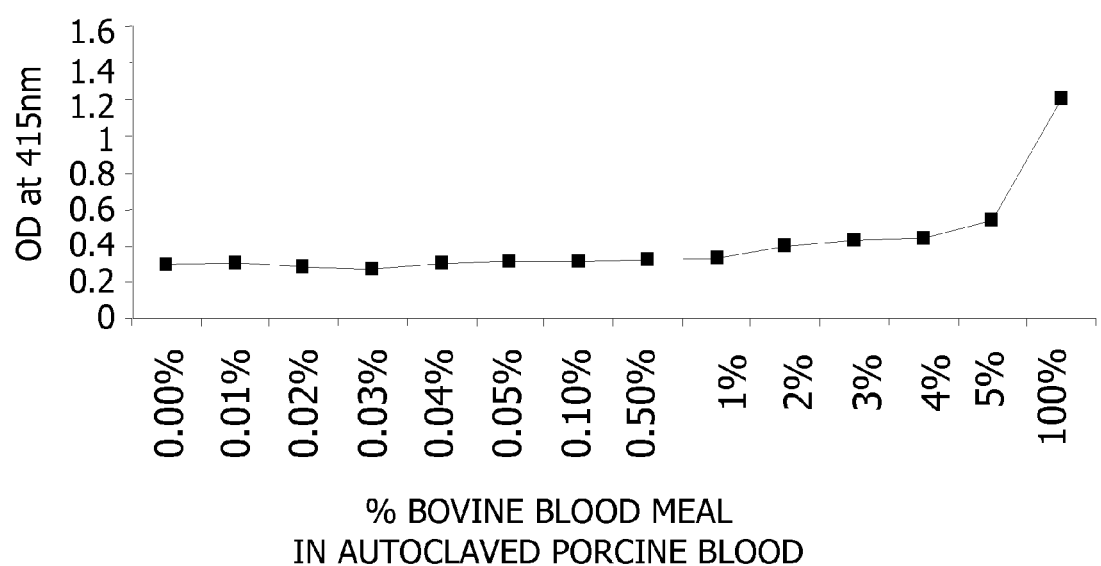
FIG. 10 is a graph depicting the detection of bovine plasma meal in autoclaved porcine blood by antibodies 6G12 (capture antibody) and 3D6 (biotin conjugated detection antibody) when used in a sandwich ELISA as more fully described in Examples 2 and 3.
Figure 11:
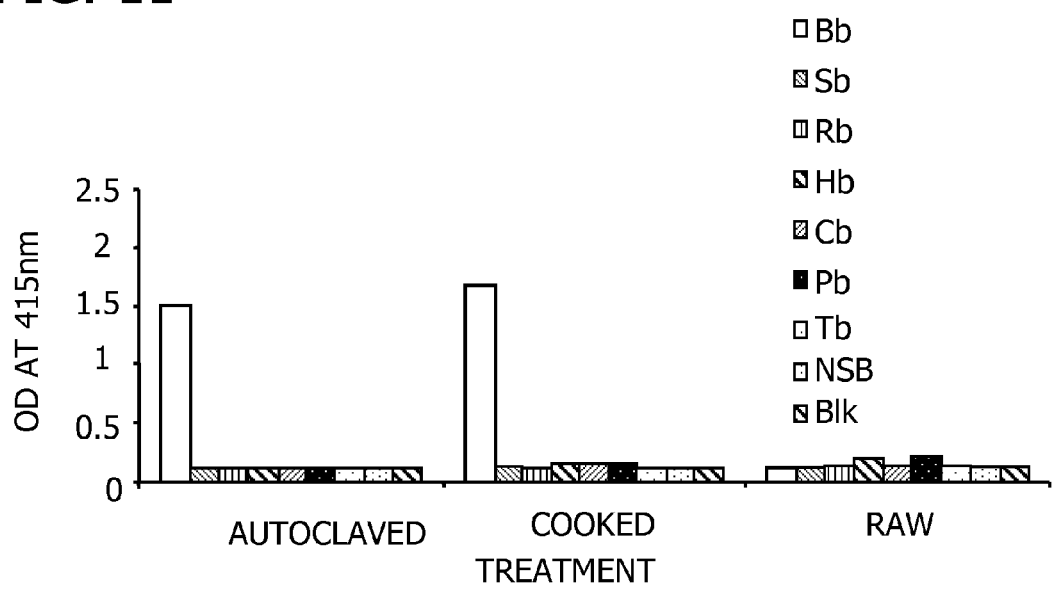
FIG. 11 is a graph depicting the effect of heat treatment on the species specificity of antibody 6E1 when used in an ELISA with soluble protein samples from autoclaved, cooked and raw meat as more fully described in Examples 2 and 3. Bb=bovine blood, Sb=sheep blood, Rb=rabbit blood, Hb=horse blood, Cb=chicken blood, Pb=pork blood, Tb=turkey blood, NSB1=nonspecific binding 1(antibody only), NSB2=nonspecific binding 2(antigen only), Blk=blank (no antibody, no antigen)
Figure 12:
FIG. 12 is a graph depicting the effect of heat treatment on the species specificity of antibody 6F10 when used in an ELISA with soluble protein samples from autoclaved, cooked and raw meat as more fully described in Examples 2 and 3. Bb=bovine blood, Sb=sheep blood, Rb=rabbit blood, Hb=horse blood, Cb=chicken blood, Pb=prok blood, Tb=turkey blood, NSB1=nonspecific binding 1(antibody only), NSB2=nonspecific binding 2(antigen only), Blk=blank (no antibody, no antigen)
Figure 14:
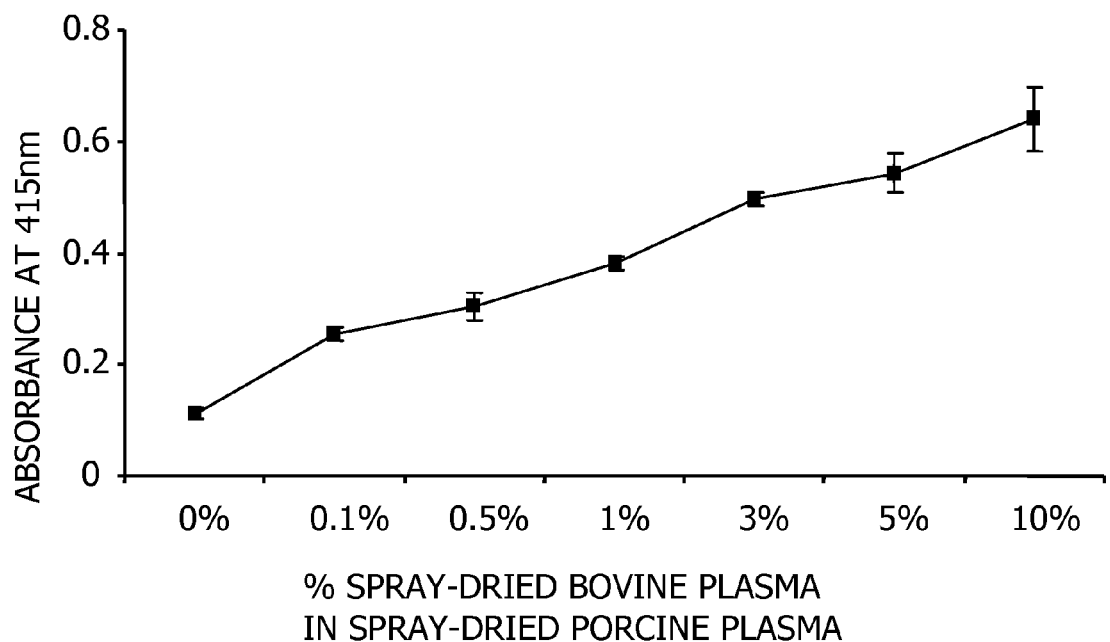
FIG. 14 is a graph depicting the detection of spray-dried bovine plasma in spray-dried porcine plasma by antibodies 6G12 (capture antibody) and 3D6 (biotin conjugated detection antibody) when used in a sandwich ELISA as more fully described in Examples 2 and 3.
Figure 15:
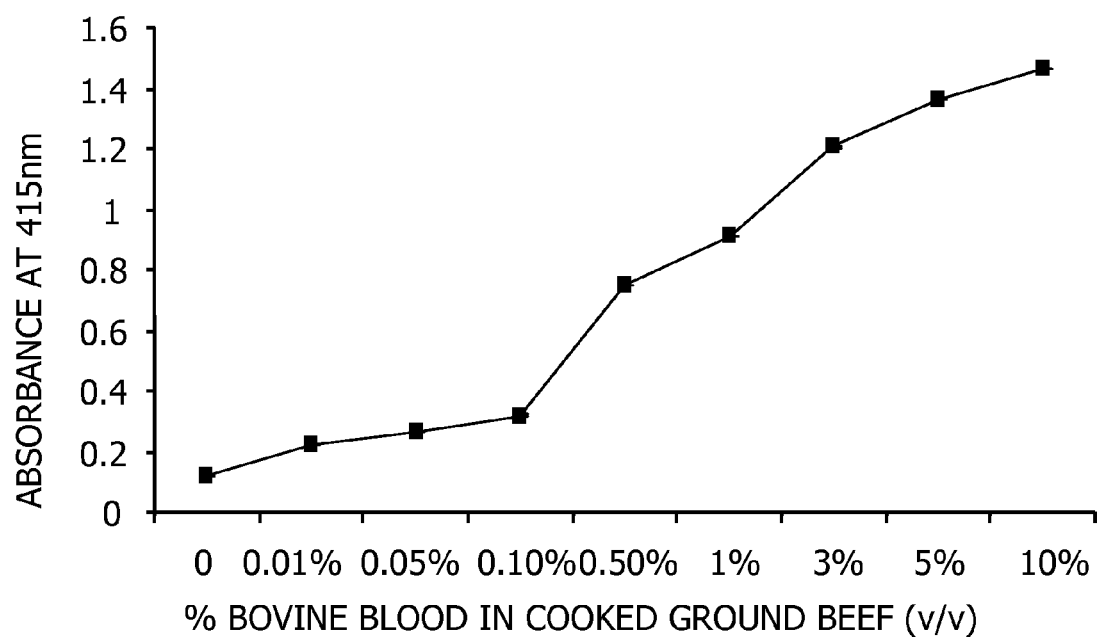
FIG. 15 is a graph depicting the detection of bovine blood in cooked ground beef (v/v) by antibodies 6G12 (capture antibody) and 3D6 (biotin conjugated detection antibody) when used in a sandwich ELISA as more fully described in Examples 2 and 3.
Figure 16:
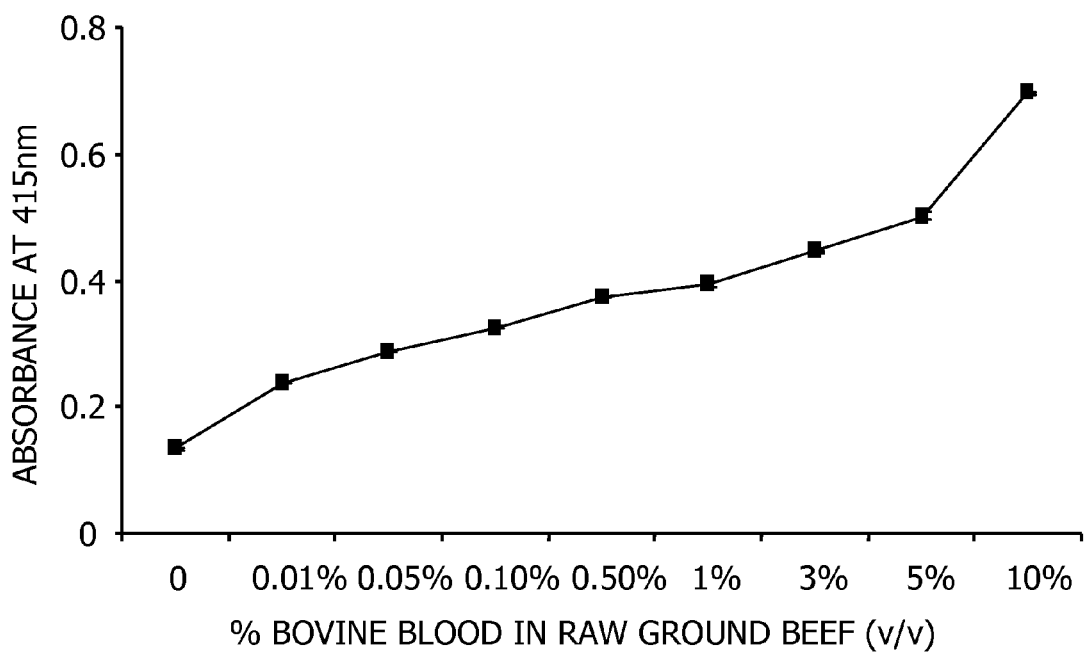
FIG. 16 is a graph depicting the detection of bovine blood in raw ground beef (v/v) by antibodies 6G12 (capture antibody) and 3D6 (biotin conjugated detection antibody) when used in a sandwich ELISA as more fully described in Examples 2 and 3.
Figure 17:
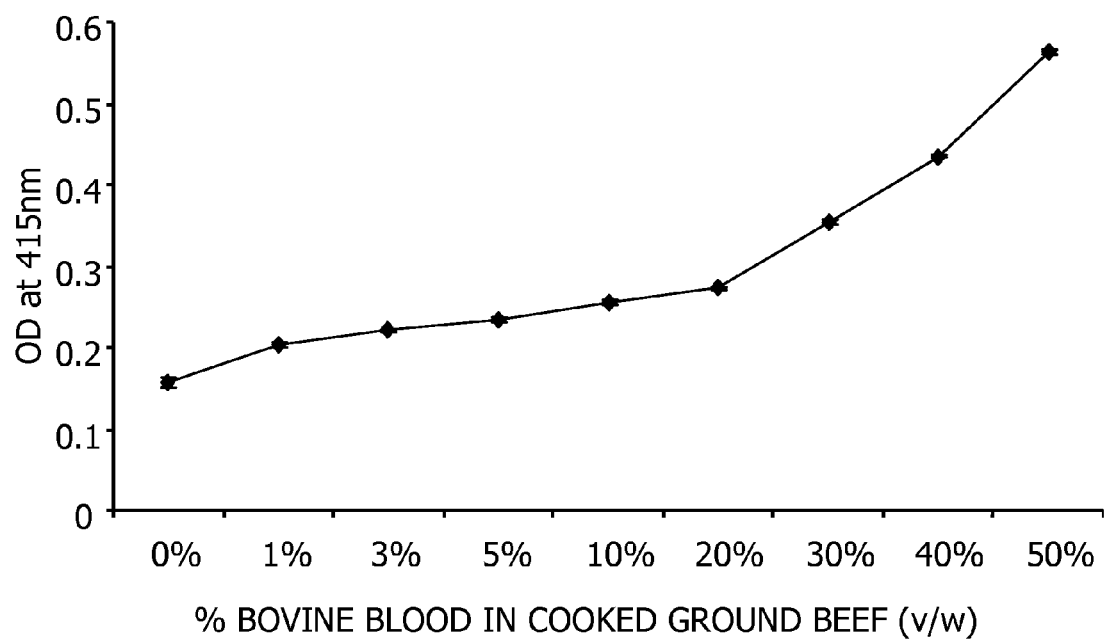
FIG. 17 is a graph depicting the detection of bovine blood in cooked ground beef (v/w) by antibodies 6G12 (capture antibody) and 3D6 (biotin conjugated detection antibody) when used in a sandwich ELISA as more fully described in Examples 2 and 3.
Figure 18:
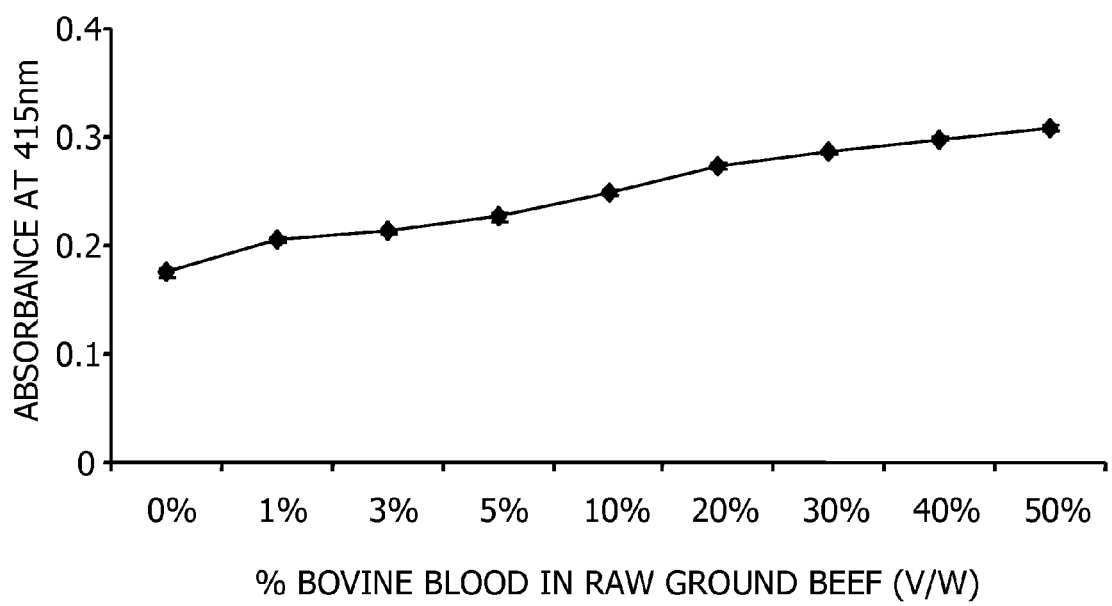
FIG. 18 is a graph depicting the detection of bovine blood in raw ground beef (v/w) by antibodies 6G12 (capture antibody) and 3D6 (biotin conjugated detection antibody) when used in a sandwich ELISA as more fully described in Examples 2 and 3.

The limit of detection is the smallest quantity of the analyte that can be reliably distinguished from the background noise in the test (Dixon 1998). This was determined using adulterated commercially produced feedstuffs as well as laboratory prepared blood samples. See, FIGS. 8-10 and 13-18.

Reproducibility is the variability between replicate determinations in the same assay (intra-assay variability) and in different assays (inter-assay variability) and this is represented as the coefficient of variation (CV). This was done using bovine blood containing samples (spray-dried bovine plasma, whole bovine blood powder, autoclaved, cooked and raw bovine blood) at levels above the detection limit.

Sensitivity is the ability of the test to detect positive samples as positive and was computed as A/B×100% where B was the number of positive samples tested and A the number of positive samples that the test was able to correctly detect as positive. Specificity is the ability of the test to detect negative samples as negative and was computed as C/D×100% where D was the number of negative samples tested and C the number of negative samples that the test was able to correctly detect as negative. Overall accuracy is the combined ability of the test to correctly detect positive and negative samples (overall accuracy=specificity and sensitivity) (Dixon 1998). This was computed as E/F×100% where F was the total number of positive and negative samples tested and E the number of positive and negative samples correctly detected by the assay. All bovine blood containing samples (spray-dried bovine plasma; whole bovine blood powder; autoclaved, cooked and raw bovine blood) at concentration levels above the detection limit were used to compute the overall accuracy of the sandwich ELISA.

Statistical Analysis

All experiments were performed in triplicate and results analyzed using Microsoft Excel 2000. One-way ANOVA using SPSS software (11.0 for Windows) (SPSS Inc., Chicago, Ill.) was used to compare means for difference among three or more treatment groups. Post-hoc analysis was performed using Tukey HSD. Paired T-test was used to compare means of background noise and detection limit. Significance was accepted at $P \leq 0.05$.

What is claimed is:

1. A monoclonal antibody which binds a thermostable antigen from bovine blood, wherein the antibody is selected from the group consisting of monoclonal antibodies 1B4, 1H9, 2B11, 3D6, 6E1, 6F10, 6G12 and 7F6 produced by hybridoma cell lines deposited as ATCC Nos. PTA-9870, PTA-9869, PTA-9868, PTA-9867, PTA-9982, PTA-9983, PTA-9985 and PTA-9984, respectively.

2. The monoclonal antibody of claim 1, wherein the antibody is 6E1.

3. The monoclonal antibody of claim 1, wherein the antibody is 6G12.

4. The monoclonal antibody of claim 1, wherein the antibody is 6F10.

5. The monoclonal antibody of claim 1, wherein the antibody is 7F6.

6. The monoclonal antibody of claim 1, wherein the antibody is 3D6.

7. A kit comprising at least one monoclonal antibody of claim 1.

8. The kit of claim 7, wherein the at least one antibody is selected from the group consisting of 3D6 and 6G12.

9. The kit of claim 7, wherein the at least one monoclonal antibody is 6E1.

10. The kit of claim 7, wherein the kit comprises two antibodies selected from the group consisting of monoclonal antibodies 1B4, 1H9, 2B11, 3D6, 6E1, 6F10, 6G12 and 7F6 produced by hybridoma cell lines deposited as ATCC Nos.

PTA-9870, PTA-9869, PTA-9868, PTA-9867, PTA-9982, PTA-9983, PTA-9985 and PTA-9984, respectively.

11. The kit of claim 10, wherein the two antibodies are 3D6 and 6G12.

12. The kit of claim 10, wherein one antibody is coated on a solid surface capable of being used in a immunoassay, and the other antibody is conjugated to a detectable marker.

13. A monoclonal antibody selected from the group consisting of monoclonal antibodies 1B4, 1H9, 2B11, 3D6, 6E1, 6F10, 6G12 and 7F6 produced by hybridoma cell lines deposited as ATCC Nos. PTA-9870, PTA-9869, PTA-9868, PTA-9867, PTA-9982, PTA-9983, PTA-9985 and PTA-9984, respectively.

* * * * *